(12) United States Patent
Park et al.

(10) Patent No.: US 11,680,270 B2
(45) Date of Patent: Jun. 20, 2023

(54) RECOMBINANT ACID-RESISTANT YEAST WITH INHIBITED LACTATE METABOLISM AND ALCOHOL PRODUCTION AND METHOD OF PRODUCING LACTIC ACID USING THE SAME

(71) Applicant: SK INNOVATION CO., LTD., Seoul (KR)

(72) Inventors: Jae Yeon Park, Daejeon (KR); Tae Young Lee, Daejeon (KR); Ki Sung Lee, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 106 days.

(21) Appl. No.: 17/064,817

(22) Filed: Oct. 7, 2020

(65) Prior Publication Data
US 2022/0049262 A1 Feb. 17, 2022

(30) Foreign Application Priority Data
Oct. 8, 2019 (KR) .................. 10-2019-0124701

(51) Int. Cl.
*C12N 15/81* (2006.01)
*C12N 1/16* (2006.01)
*C12P 7/56* (2006.01)

(52) U.S. Cl.
CPC .............. *C12N 15/81* (2013.01); *C12N 1/16* (2013.01); *C12P 7/56* (2013.01)

(58) Field of Classification Search
CPC ........ C12N 1/185; C12N 9/88; C12N 15/815; C12Y 101/01001; C12P 7/56
See application file for complete search history.

(56) References Cited

U.S. PATENT DOCUMENTS

| | | | |
|---|---|---|---|
| 7,049,108 B2 | 5/2006 | Porro et al. | |
| 7,141,410 B2 | 11/2006 | Rajgarhia et al. | |
| 7,232,664 B2 | 6/2007 | Van Hoek et al. | |
| 7,534,597 B2 | 5/2009 | Hause et al. | |
| 8,137,953 B2 | 3/2012 | Miller et al. | |
| 9,353,388 B2 | 5/2016 | Kim et al. | |
| 9,617,570 B2 * | 4/2017 | Lim | C12N 15/01 |
| 9,758,770 B2 * | 9/2017 | Lim | C07K 14/39 |
| 2003/0032152 A1 | 2/2003 | Porro et al. | |
| 2003/0190630 A1 | 10/2003 | Rajgarhia et al. | |
| 2009/0053782 A1 | 2/2009 | Dundon et al. | |
| 2012/0058529 A1 | 3/2012 | Ikushima et al. | |
| 2012/0214214 A1 | 8/2012 | Hara et al. | |
| 2012/0295319 A1 | 11/2012 | Nevoigt et al. | |
| 2013/0071893 A1 | 3/2013 | Lynch et al. | |
| 2015/0064752 A1 | 3/2015 | Lee et al. | |
| 2015/0152447 A1 | 6/2015 | Kim et al. | |
| 2016/0024484 A1 | 1/2016 | Lim et al. | |
| 2016/0333380 A1 | 11/2016 | Chung et al. | |
| 2021/0155945 A1 | 5/2021 | Park et al. | |
| 2021/0324346 A1 | 10/2021 | Park et al. | |
| 2021/0403882 A1 | 12/2021 | Park et al. | |
| 2022/0056459 A1 | 2/2022 | Park et al. | |

FOREIGN PATENT DOCUMENTS

| | | |
|---|---|---|
| EP | 2873725 A1 | 5/2015 |
| EP | 3795689 A1 | 3/2021 |
| EP | 3865577 A2 | 8/2021 |
| EP | 3896166 A1 | 10/2021 |
| JP | 2001204464 A | 7/2001 |
| JP | 2005137306 A | 6/2005 |
| JP | 4095889 B2 | 6/2008 |
| JP | 4692173 B2 | 6/2011 |
| JP | 4700395 B2 | 6/2011 |
| KR | 101576186 B1 | 12/2015 |
| KR | 1020160012561 A | 2/2016 |
| KR | 1020160133308 A | 11/2016 |
| KR | 101686900 B1 | 12/2016 |
| KR | 1020170008151 A | 1/2017 |
| KR | 1020170025315 A | 3/2017 |
| KR | 1020170077599 A | 7/2017 |
| KR | 1020180015591 A | 2/2018 |
| KR | 1020190121030 A | 10/2019 |
| KR | 1020190121031 A | 10/2019 |
| KR | 102140596 B1 | 8/2020 |
| KR | 1020210128742 A | 10/2021 |
| WO | 9914335 A1 | 3/1999 |
| WO | 2005052174 A3 | 6/2005 |
| WO | 2007117282 A2 | 10/2007 |
| WO | 2019203436 A1 | 10/2019 |
| WO | 2020075986 A2 | 4/2020 |

OTHER PUBLICATIONS

Ellen I. Garvie, Microbiological Reviews, 106-139, 1980.
Michael Sauer et al., Biotechnology and Genetic Engineering Reviews, 27:229-256, 2010.
Andrew P. Halestrap, The monocarboxylate transporter family—Structure and Functionals Characterization, IUBMB Life, 64(1):1-9, 2012.
António Pacheco et al., Lactic acid production in *Saccharomyces cerevisiae* is modulated by expression of the monocarboxylate transporter Jen1 and Ady2, FEMS Yeast Res. 12 (2012) 375-381.
Minoska Valli et al., Improvement of Lactic acid production in *Saccharomyces cerevisiae* by cell sorting for high intracellular pH, Appl Environ Microbiol. 2006 72(8): 5492-5499.
Guiard, B., Structure, expression and regulation of a nuclear gene encoding a mitochondrial protein: the yeast L(+)-lactate cytochrome c oxidoreductase (cytochrome b2), EMBO J., 4, 3265-3272 (1985).

(Continued)

*Primary Examiner* — Tekchand Saidha
(74) *Attorney, Agent, or Firm* — The Webb Law Firm

(57) ABSTRACT

Disclosed is a method of producing lactic acid using a recombinant acid-resistant yeast with inhibited lactate metabolism and alcohol production. More specifically, disclosed are a recombinant acid-resistant yeast in which lactate consumption reaction is reduced and which is imparted with lactic-acid-producing ability to thereby exhibit improved lactic-acid-producing ability and reduced ethanol production, and a method of producing lactic acid using the same.

3 Claims, 3 Drawing Sheets

Specification includes a Sequence Listing.

(56) References Cited

OTHER PUBLICATIONS

Lodi, T., and Ferrero, I., Isolation of the DLD gene of *Saccharomyces cerevisiae* encoding the mitochondrial enzyme D-lactate ferricytochrome c oxidoreductase. Mol. Gen. Genet., 238, 315-324 (1993).
Aki Ookubo et al., Improvement of L-lactate production by CYB2 gene disruption in a Recombinant *Saccharomyces cerevisiae* Strain under low pH condition, Biosci. Biotechnol. Biochem., 72(11), 3063-3066, 2008.
Antonius J. A. van Maris et al., Mini-review Microbial export of lactic and 3-hydroxypropanoic acid: implication for industrial fermentation processes, Metabolic Engineering 6 (2004) 245-255.
European Search Report from Corresponding EP Application No. 20 20 0641 dated Mar. 19, 2021.
Hyland, P., "Development of a Platform Strain for Production of Adipic Acid Yields Insights into the Localized Redox of Metabolism of *S. cerevisiae*". Dissertation, University of Toronto, 2013.
Jiang et al., "Progress of succinic acid production from renewable resources: metabolic and fermentative strategies", Bioresource Technology, 2017, pp. 1-38.
Karlin et al., "Applications and statistics for multiple high-scoring segments in molecular sequences", Proceedings of the National Academy of Sciences, 1993, pp. 5873-5877, vol. 90, No. 12.
Nishant et al., "The baker's yeast diploid genome is remarkably stable in vegetative growth and meiosis", PLoS Genet, 2010, pp. 1-15, vol. 6, No. 9 e1001109.
Steiger et al., "Biochemistry of microbial itaconic acid production", Frontiers in Microbiology, 2013, pp. 1-5, vol. 4, No. 23.
Storchova, Z., "Ploidy changes and genome stability in yeast", Yeast, 2014, pp. 421-430, vol. 31, No. 11.
Zelle et al., "Malic acid production by *Saccharomyces cerevisiae*: engineering of pyruvate carboxylation, oxaloacetate reduction, and malate export", Applied and Environmental Microbiology, 2008, pp. 2766-2777, vol. 74, No. 9.
Zhang et al., "A synthetic metabolic pathway for production of the platform chemical isobutyric acid", ChemSusChem, 2011, pp. 1068-1070, vol. 4, No. 8.
Abbott et al., "Metabolic engineering of *Saccharomyces cerevisiae* for production of carboxylic acids: current status and challenges", FEMS Yeast Research, 2009, pp. 1123-1136, vol. 9.
Albertyn et al., "GPD1, which encodes glycerol-3-phosphate dehydrogenase, is essential for growth under osmotic stress in *Saccharomyces cerevisiae*, and its expression is regulated by the high osmolarity glycerol response pathway". Molecular and cellular biology, 1994, pp. 4135-4144, vol. 14, No. 6.
Baek et al., "Metabolic engineering and adaptive evolution for efficient production of D-lactic acid in *Saccharomyces cerevisiae*", Applied Microbiology and Biotechnology, 2016, pp. 2737-2748, vol. 100.
Costenoble et al. "Microaerobic glycerol formation in *Saccharomyces cerevisiae*", Yeast, 2000, pp. 1483-1495, vol. 16.
Devos et al., "Practical Limits of Function Prediction" Proteins: Structure, Function and Genetics, 2000, pp. 98-107, vol. 41.
Dexter et al., "Robust network structure of the Sln1-Ypd1-Ssk1 three-component phospho-relay prevents unintended activation of the HOG MPAK pathway in *Saccharomyces cerevisiae*", BMC Systems Biology, 2015, pp. 1-15, vol. 9, No. 17.
Feldman-Salit et al., "Regulation of the activity of lactate dehydrogenases from four lactic acid bacteria" Journal of Biological Chemistry 288.29 (2013), pp. 21295-21306.
Hoppner et al., "Purification and kinetic characteristics of pyruvate decarboxylase and ethanol dehydrogenase from Zymomonas mobilis in relation to ethanol production", European Journal of Applied Microbiology and Biotechnology, 1983, pp. 152-157, vol. 17.
Hubmann et al., "Identification of multiple interacting alleles conferring low glycerol and high ethanol yield in *Saccharomyces cerevisiae* ethanolic fermentation", Biotechnology for Biofuels, 2013,pp. 1-17, vol. 6, No. 87.

Hubmann et al., "Quantitative trait analysis of yeast biodiversity yields novel gene tools for metabolic engineering," Metabolic Engineering, 2013, pp. 68-81, vol. 17.
Kisselev, L., "Polypeptide Release Factors in Prokaryotes and Eukaryotes: Same Function, Different Structure" Structure, 2002, pp. 8-9, vol. 10.
NCBI, GenBank Accession No. SMN19920.1, similar to *Saccharomyces cerevisiae* YLR044C PDC1 Major of three pyruvate decarboxylase isozymes, key enzyme in alcoholic fermentation, decarboxylates pyruvate to acetaldehyde [Kazachstania saulgeensis], 2017.
Nevoigt et al., "Osmoregulation and glycerol metabolism in the yeast *Saccharomyces cerevisiae*", FEMS Microbiology Reviews, 1997, pp. 231-241, vol. 21.
Ishida et al., "Efficient production of L-lactic acid by metabolically engineered *Saccharomyces cerevisiae* with a genome-integrated L-lactate dehydrogenase gene", Applied and Environmental Microbiology, 2005, pp. 1964-1970, vol. 71, No. 4.
Park et al., "Low-pH production of D-lactic acid using newly isolated acid tolerant yeast Pichia kudriavzevii NG7", Biotechnology and Bioengineering, 2018, pp. 2232-2242, vol. 115.
Pearson, "Effective protein sequence comparison", Methods Enzymology, 1996, pp. 227-258, vol. 266.
Savijoki et al., "Molecular genetic characterization of the L-lactate dehydrogenase gene (IdhL) of Lactobacillus helveticus and biochemical characterization of the enzyme" Applied and Environmental Microbiology,(1997), pp. 2850-2856, vol. 63, No. 7.
Shen et al., "Effect on electrospun fibres by synthesis of high branching polylactic acid," R. Soc. Open Sci., 2018, pp. 1-13, vol. 5.
Skory et al., "Inhibition of Rhizopus lactate dehydrogenase by fructose 1,6-bisphosphate" Enzyme and Microbial Technology 44 (2009): 242-247.
Tokuhiro et al., "Double mutation of the PDC1 and ADH1 genes improves lactate production in the yeast *Saccharomyces cerevisiae* expressing the bovine lactate dehydrogenase gene" Applied Microbiology and Biotechnology 82.5 (2009): pp. 883-890.
Uniprot, Accession No. A0A1X7R452, 2019, www.uniprot.org.
Whisstock et al., "Prediction of protein function from protein sequence and structure" Quarterly Reviews of Biophysics, 2003, pp. 307-340, vol. 36, No. 3.
Witkowski et al., "Conversion of a Beta-Ketoacyl Synthase to a Malonyl Decarboxylase by Replacement of the Active-Site Cysteine with Glutamine" Biochemistry, 1999, pp. 11643-11650, vol. 38.
Zhang et al., "Adaptive mutations in sugar metabolism restore growth on glucose in a pyruvate decarboxylase negative yeast strain" Microbial Cell Factories 14, (2015): article 116, pp. 11 pages.
Skory et al., "Lactic acid production by *Saccharomyces cerevisiae* expressing a Rhizopus oryzae lactate dehydrogenase gene", Journal of Industrial Microbiology and Biotechnology, 2003, pp. 22-27, vol. 30, No. 1.
Abbott et al., "Catalase Overexpression Reduces Lactic Acid-Induced Oxidative Stress in *Saccharomyces cerevisiae*", Applied and Environmental Microbiology, 2009, pp. 2320-2325, vol. 75, No. 8.
Fletcher et al.,. "Evolutionary engineering reveals divergent paths when yeast is adapted to different acidic environments", Metabolic Engineering, 2017, pp. 1-37.
Gao et al., "Zinc finger protein 637 protects cells against oxidative stress-induced premature senescence by mTERT-mediated telomerase activity and telomere maintenance", Cell Death and Disease, 2014, pp. 1-13, vol. 5, No. e1334.
GenEmbl Accession No. CP024408, 2017.
Lee et al., "Co-expression of two heterologous lactate dehydrogenases genes in Kluyveromyces marxianus for L-lactic acid production", J. Biotechnology, 2017, pp. 81-86, vol. 241.
Long et al., "How adaptive evolution reshapes metabolism to improve fitness: recent advances and future outlook" Current Opinion in Chemical Engineering, 2018, pp. 209-215, vol. 22.
Prasad et al., "Molecular Mechanisms of Zinc as a Pro-Antioxidant Mediator: Clinical Therapeutic Implications", Antioxidants, 2019, pp. 1-22, vol. 8, No. 164.

(56) References Cited

OTHER PUBLICATIONS

Van Maris et al., "Homofermentative Lactate Production Cannot Sustain Anaerobic Growth of Engineered *Saccharomyces cerevisiae*: Possible Consequence of Energy-Dependent Lactate Export", Appl. Environ. Microbiol., 2004, pp. 2898-2905, vol. 70, No. 5.

Zhu et al., "Evolutionary engineering of industrial microorganims-strategies and applications", Applied Microbiology and Biotechnology, 2018, pp. 4615-4627.

Zhou et al., "Selective Sensitization of Zinc Finger Protein Oxidation by ROS Through Arsenic Binding", The Journal of Biological Chemistry, 2015, pp. 18361-18369, vol. 290.

* cited by examiner

RECOMBINANT ACID-RESISTANT YEAST WITH INHIBITED LACTATE METABOLISM AND ALCOHOL PRODUCTION AND METHOD OF PRODUCING LACTIC ACID USING THE SAME

CROSS REFERENCE TO RELATED APPLICATIONS

This application claims priority to KR patent application No. 10-2019-0124701, filed Oct. 8, 2019, which is incorporated herein by reference thereto.

SEQUENCE LISTING

The instant application contains a Sequence Listing which has been submitted in ASCII format via EFS-Web and is hereby incorporated by reference in its entirety. Said ASCII copy, created on Oct. 7, 2021, is named PF-B2455_ST25-10-7-2021.txt and is 27,283 bytes in size.

BACKGROUND OF THE INVENTION

Field of the Invention

The present invention relates to a recombinant acid-resistant yeast with inhibited lactate metabolism and alcohol production and a method of producing lactic acid using the same, and more particularly to a recombinant acid-resistant yeast in which lactate consumption reaction is reduced and to which lactic-acid-producing ability is imparted, thereby exhibits improved lactic-acid-producing ability and ethanol production is inhibited, and a method of producing lactic acid using the same.

Description of the Related Art

A traditional lactic acid production process is performed using lactic acid bacteria, and includes conducting fermentation while maintaining a neutral pH of 6 to 8 using various forms of Ca salt, Mg salt, or neutralizing agent such as ammonia in order to prevent bacterial death or stop growth due to the accumulation of lactic acid produced by lactic acid bacteria. When fermentation is completed, microorganisms are separated, and sulfuric acid is added to convert lactate to lactic acid while Ca salt is removed in the form of $CaSO_4$ due to the difficulty of separation of salt from water and conversion thereof to lactide. In this process, $CaSO_4$, a byproduct, is produced in an amount greater than the amount of lactic acid, thus deteriorating process efficiency.

Polylactic acid (PLA) is a biodegradable polymer that is prepared by converting lactic acid into lactide and conducting ring-opening polymerization thereon. The raw material, lactic acid, is produced through fermentation. PLA is widely useable in disposable food containers, and has strength that enables use alone or in the form of a composition or a copolymer in plastics for a variety of industries including the automobile industry. In addition, it is a representative polymer that has been used in 3D printing in recent years, and is an eco-friendly polymer that generates lower amounts of harmful gas and odor when used for 3D printers.

Meanwhile, lactic acid has L- and D-type optical isomers. There are a variety of microbial groups. For example, lactic acid bacteria that mainly produce L-type optical isomers often also produce about 5-10% of D-type optical isomers, and strains that mainly produce D-type optical isomers include strains that produce both D-type and L-type optical isomers, strains that produce both D-type optical isomers and ethanol and the like (Ellen I. Garvie, *Microbiological Reviews*, 106-139, 1980).

In general, PLA produces lactic acid through fermentation, and then converts the produced lactic acid into lactide through a purification process. For conversion to lactide, a process of converting lactic acid into a hydrogenated form is required, and the pH is generally in a neutral range from 6 to 7 for fermentation, and the neutral pH is thus changed to acidic pH using a large amount of sulfuric acid. In this process, a large amount of neutralization salts is generated, and economic feasibility is deteriorated due to the low value of the neutralization salts along with the cost of investing in processes to remove these neutralization salts.

Meanwhile, in the case of *Lactobacillus*, which produces lactic acid in nature, a large amount of expensive nutrients must be used as a medium to commercially produce lactic acid. This excess of nutrient components greatly inhibits a downstream polymerization process, or the lactide conversion process in the case in which lactide is used as an intermediate, and costs for purification processes such as adsorption, distillation and ion exchange are incurred in order to obtain high-yield and high-purity polymers or precursors thereof, thus further increasing production costs. Research using yeast has been suggested in order to solve these problems. Yeast is known to conduct growth/fermentation even when inexpensive nutrients are used, and to be highly resistant to acidic conditions.

When lactic acid is produced using yeast that grows well under the acidic condition (hereinafter referred to as "acid-resistant yeast"), the fermentation process is simplified because it is not necessary to maintain the medium at a pH of 6 to 7 using a neutralizing agent during fermentation, and a downstream purification process for removing the neutralizing agent is not required. In addition, yeast itself produces many components that it requires for metabolism, and thus can be cultured in a medium with a relatively low nutrient level compared to bacteria, particularly *Lactobacillus*, thus enabling downstream purification processes to be omitted and significantly lowering production costs.

However, there is a prerequisite for technology for producing lactic acid using yeast. The prerequisite is that the yield, productivity, and concentration of lactic acid, which are indicators for strain fermentation performance, must be maintained at a high level similar to the performance of lactic acid bacteria in order for the technology to be commercially applied.

Although the development of acid-resistant lactic acid technology using yeast has been attempted, in practice, in many cases, high-performance fermentation capability is obtained only when fermentation is performed while maintaining the pH of at least 3.7, which is not less than the pKa value of lactic acid, by performing a neutralization reaction during the fermentation. For this reason, it is not reasonable to determine that the technology is a practical acid-resistance method, and it is difficult to anticipate an effect of reducing production costs when applied to a process (Michael Sauer et al., *Biotechnology and Genetic Engineering Reviews*, 27:229-256, 2010).

Therefore, acid-resistant yeasts capable of reducing processing costs can realize commercial application only when they must be capable of completing fermentation at a pH of a fermentation broth not more than the pKa value, without using a neutralizing agent or using the same in a minimum amount, and three major fermentation indicators achieve a level similar to that of lactic acid bacteria.

In general, yeast metabolizes ethanol as a main product when glucose is fermented, and hardly produces lactic acid. In addition, since the probability of selecting a strain that produces lactic acid from microorganisms having high acid resistance is very low, the present inventors selected a yeast strain having excellent acid resistance, and attempted to produce a strain exhibiting both high lactic acid production ability and inhibited ethanol production ability from the selected strain through a genetic engineering method.

Accordingly, the present inventors have made intensive efforts to produce an acid-resistant strain having lactic acid production ability but inhibited ethanol production ability. As a result, the present inventors produced a recombinant strain by removing a gene involved in the reaction for converting lactate to pyruvate from an acid-resistant yeast and additionally introducing a gene encoding lactate dehydrogenase into the yeast, and found that lactic acid production ability was improved and ethanol production ability was inhibited when producing lactic acid using the recombinant strain. Based on this finding, the present invention has been completed.

SUMMARY OF THE INVENTION

Therefore, the present invention has been made in view of the above problems, and it is one object of the present invention to provide a recombinant acid-resistant yeast strain having improved lactic acid production ability and reduced ethanol production ability.

It is another object of the present invention to provide a method of producing lactic acid using the recombinant acid-resistant yeast.

It is another object of the present invention to provide a gene having enzymatic activity that converts lactate derived from the acid-resistant yeast into pyruvate.

It is another object of the present invention to provide a promoter capable of inducing gene expression by lactic acid that can be used in the production of recombinant strains having lactic acid production ability.

In accordance with one aspect of the present invention, the above and other objects can be accomplished by the provision of a recombinant strain having lactic-acid-producing ability, in which a gene encoding an enzyme converting lactate to pyruvate is deleted or attenuated from an acid-resistant yeast YBC strain (KCTC13508BP), and a gene encoding a lactate dehydrogenase is introduced into the YBC strain.

In accordance with another aspect of the present invention, there is provided a recombinant strain having lactic-acid-producing ability, a g2947 gene, which is a gene encoding an enzyme converting lactate into pyruvate, a g4423 gene, which is a gene encoding an alcohol dehydrogenase, and a g3002 gene, which is a gene encoding a pyruvate decarboxylase are deleted from an acid-resistant yeast YBC strain (KCTC13508BP), and a gene encoding a lactate dehydrogenase is introduced into the strain.

In accordance with another aspect of the present invention, there is provided a method of producing lactic acid including (a) culturing the recombinant strain according to the present invention to produce lactic acid, and (b) obtaining the produced lactic acid.

In accordance with another aspect of the present invention, there is provided a gene encoding a protein having enzymatic activity of converting lactate to pyruvate and having an amino acid sequence represented by SEQ ID NO: 3 or SEQ ID NO: 4.

In accordance with another aspect of the present invention, there is provided a protein having enzymatic activity of converting lactate to pyruvate and having an amino acid sequence represented by SEQ ID NO: 3 or SEQ ID NO: 4.

In accordance with another aspect of the present invention, there is provided a promoter of a g2947 gene having a nucleotide sequence represented by SEQ ID NO: 5 or SEQ ID NO: 6.

Effects of the Invention

The recombinant acid-resistant yeast according to the present invention inhibits ethanol production to inhibit the conversion of lactate to pyruvate in the cell, and strongly expresses an LDH enzyme to produce lactic acid at high yield.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
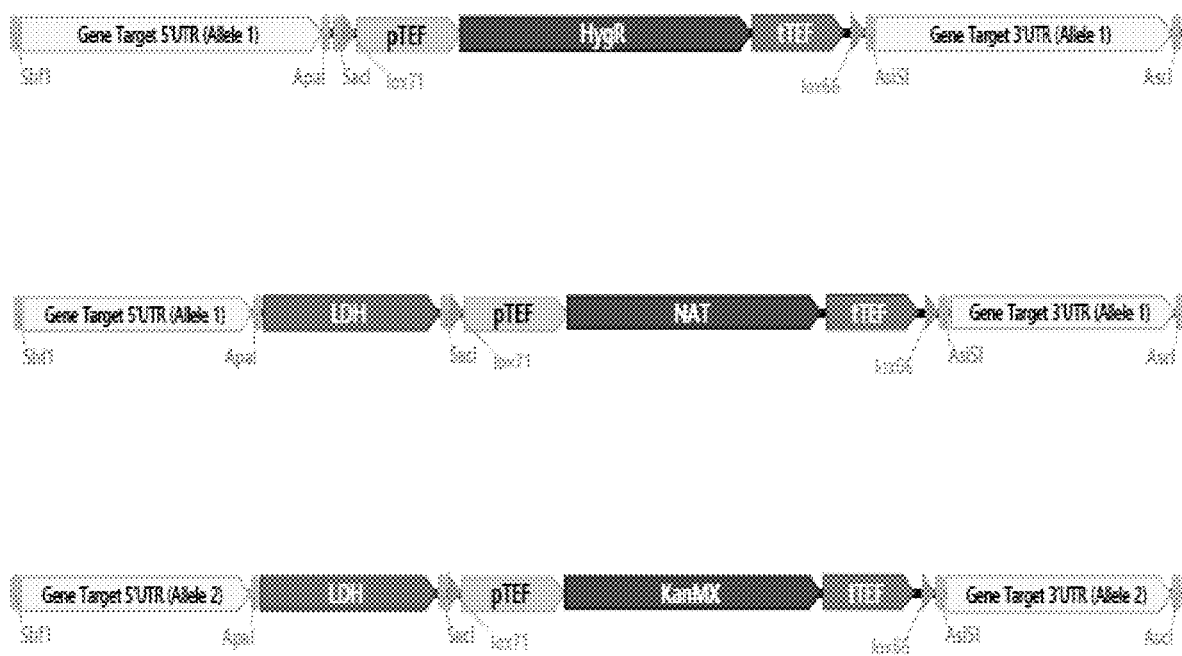
FIG. 1 shows a deletion cassette used to delete a g2947 gene from the genome of a YBC or YBC2 strain and insert a LDH gene into the genome according to the present invention.

Unless defined otherwise, all technical and scientific terms used herein have the same meanings as appreciated by those skilled in the field to which the present invention pertains. In general, the nomenclature used herein is well-known in the art and is ordinarily used.

Acid-resistant yeast is characterized by consuming sugar at a fast rate even at an acidic pH, exhibiting a high growth rate, and converting the consumed sugar into a desired product under fermentation conditions. The present inventors selected the acid-resistant yeast YBC strain (KCTC13508BP) from among yeasts having these characteristics through several yeast libraries, and the acid-resistant yeast YBC strain (KCTC13508BP) has high growth and sugar consumption rate even at a lactic acid concentration of 40 g/L to 80 g/L. By controlling a metabolic circuit to increase the ability to produce lactic acid and lower the ability to produce ethanol of the acid-resistant yeast YBC strain, a gene encoding an enzyme that converts lactate into pyruvate was deleted from a YBC strain from which a gene encoding alcohol dehydrogenase and a gene encoding pyruvate decarboxylase are deleted and into which a lactate dehydrogenase gene was introduced, thereby producing a recombinant strain, and the fact that the recombinant strain had high lactic acid production ability and inhibited ethanol production ability was confirmed.

Therefore, in one aspect, the present invention is directed to a recombinant strain having lactic-acid-producing ability, in which a gene encoding an enzyme converting lactate to pyruvate is deleted or attenuated from an acid-resistant yeast YBC strain (KCTC13508BP), and a gene encoding a lactate dehydrogenase is introduced into the YBC strain.

Two methods for suppressing the lactate consumption reaction of the YBC strain (KCTC13508BP) may be considered. The first method is to find a transporter that introduces lactate from outside into the cell and remove the same, and the second method is to find an enzyme (lactate dehydrogenase) that converts lactate to pyruvate and remove the same. Many monocarboxylase transporter families have been studied, and in typically actively studied yeast, Ady2, Jen1, and the like are known to function to transport lactate from the outside (Ref: Antonio Pacheco et al., *FEMS Yeast Res.* 12 (2012) 375-381). However, in the case of fermentation using an acid-resistant strain, as in the present invention, most of the lactate, specifically about 80% to 90% thereof, is present in a hydrogenated form, namely lactic acid, at a pH of 3, although the pH may vary depending on culture conditions and on the composition of fermentation broth due to the transport by the transporter and the low external pH, and it is known that such lactic acid is transferred in the absence of a charge to the inside of the cell by direct mass transfer through the cell membrane, not transfer via the transporter (Minoska Valli et al., *Appl. Environ. Microbio.*, 72:5492, 2006). In addition, some monocarboxylate transporters function to transport the dissociated salt from the inside of the cell to the outside thereof to reduce acid stress in the cell. Therefore, the stress caused by lactic acid may be rather increased depending on the type of transporter.

Therefore, according to the present invention, based on the estimation that the effect of inhibiting the transport of lactic acid to the inside by removal of the transporter will not be significant, a strain was produced by removing the enzyme that is mainly responsible for the reaction of directly converting lactate to pyruvate inside the cell.

As enzymes and/or genes that convert lactate to pyruvate in yeast, the CYB2 gene for L-lactate and the DLD1 gene for D-lactate, respectively, are known (Guiard, B., *EMBO J.*, 4:3265, and 1985; Lodi, T., and Ferrero, I., *Mol. Gen. Genet.*, 238:315, 1993), and each of these genes has functions of converting the corresponding lactate to pyruvate in the mitochondrial membrane.

In addition, CYB2 was determined as the target gene based on a report that, when CYB2 related to L-lactate is removed, the consumption of produced lactate can be suppressed, thus increasing the fermentation yield of lactic acid (Aki Ookubo et al., *Biosci. Biotechnol. Biochem.*, 72:3063, 2008).

In one embodiment of the present invention, the main ADH gene, namely the g4423 gene, was removed from the YBC strain, the LDH gene of SEQ ID NO: 28 derived from *Lactobacillus plantarum* was introduced at the position of g4423, the g3002 gene (hereinafter referred to as "g3002-1 gene") was removed, and the LDH gene was introduced at the position of the g3002 gene to produce a recombinant strain YBC2, a g2947 gene was removed again from the recombinant strain YBC2, and an LDH gene was introduced to produce a recombinant strain YBC4, and the recombinant strains were cultured. As a result, the recombinant strains are found to have improved lactic acid production ability and reduced ethanol production ability.

In the present invention, the gene encoding the enzyme that converts lactate to pyruvate may be a g2947 gene.

In the present invention, the g2947 gene may have a nucleotide sequence represented by SEQ ID NO: 1 or SEQ ID NO: 2.

In the present invention, the recombinant strain may be characterized in that the gene encoding alcohol dehydrogenase (ADH gene) is further deleted, and the gene encoding the alcohol dehydrogenase is a g4423 gene. In the present invention, the recombinant strain may be characterized in that an LDH gene is additionally introduced, instead of the ADH gene.

In the present invention, the recombinant strain may be characterized in that a gene (PDC gene) encoding pyruvate decarboxylase is further deleted, and the gene encoding pyruvate decarboxylase is a g3002 gene.

In the present invention, the recombinant strain may be characterized in that an LDH gene is additionally introduced, instead of the PDC gene.

In the present invention, the gene encoding the lactate dehydrogenase may be introduced by substitution with the g2947 gene, and may be regulated by a promoter of the g2947 gene.

In the present invention, the recombinant strain may be characterized in that lactic-acid-producing ability is increased and ethanol-producing ability is reduced or removed compared to the parent strain, the YBC strain (KCTC13508BP), due to deletion or attenuation of the g2947 gene.

In the present invention, the gene encoding the introduced lactate dehydrogenase is preferably an LDH gene derived from *L. helveticus*, an LDH gene derived from *R. oryzae*, or an LDH gene derived from *L. plantarum*, more preferably a LDH gene derived from *L. plantarum*.

Accordingly, in another aspect, the present invention is directed to a recombinant strain having lactic-acid-producing ability, in which a g2947 gene, which is a gene encoding an enzyme converting lactate into pyruvate, a g4423 gene, which is a gene encoding an alcohol dehydrogenase, and a g3002 gene, which is a gene encoding a pyruvate decarboxylase, are deleted from an acid-resistant yeast YBC strain (KCTC13508BP), and a gene encoding a lactate dehydrogenase is introduced into the strain.

According to the present invention, the gene encoding the lactate dehydrogenase may be introduced by substitution with at least one of the g2947 gene, the g4423 gene and the g3002 gene, and may be regulated by a promoter of the substituted gene.

In one embodiment of the present invention, the YBC4 strain (Δg4423::ldh/Δg3002-1::ldh/Δg2947::ldh) was found to have significantly increased lactic acid fermentation yield compared to the YBC2 strain (Δg4423::ldh/Δg3002-1::ldh). Moreover, the YBC4 strain was found to have ethanol fermentation yield decreased by more than 90% compared to the YBC2 strain, indicating that all carbon flux was converted from ethanol to lactic acid and the yield of lactic acid increased to 84% of a theoretical value (see Table 2 and FIG. 2).

Accordingly, in another aspect, the present invention is directed to a method of producing lactic acid including (a) culturing the recombinant strain to produce lactic acid, and (b) obtaining the produced lactic acid.

Through the present invention, it is possible to obtain an acid-resistant strain exhibiting greatly increased lactate production and greatly decreased ethanol production.

In another aspect, the present invention is directed to a gene encoding a protein having activity of converting lactate to pyruvate and having 90% homology with the nucleotide sequence of SEQ ID NO: 1 or SEQ ID NO: 2.

In another aspect, the present invention is directed to a gene encoding a protein having enzymatic activity of converting lactate to pyruvate and having an amino acid sequence represented by SEQ ID NO: 3 or SEQ ID NO: 4.

In the present invention, the gene has a nucleotide sequence represented by SEQ ID NO: 1 or SEQ ID NO: 2.

In another aspect, the present invention is directed to a protein having the activity of converting lactate to pyruvate and having an amino acid sequence represented by SEQ ID NO: 3 or SEQ ID NO: 4.

In another aspect, the present invention is directed to a promoter of the g2947 gene having a nucleotide sequence represented by SEQ ID NO: 5 or SEQ ID NO: 6.

The promoter of the g2947 gene (CYB2) of the present invention can induce expression of the LDH gene in a strain producing lactic acid in the recombinant yeast according to the present invention, which is a promoter that is different from promoters that are strongly expressed at the beginning of culture under glucose-rich conditions and are strongly expressed in general glycolysis conditions, can continuously maintain the ability of cells to produce lactic acid by expressing the LDH gene at the end of culture, and is highly useful for the production of highly efficient lactic-acid-producing strains.

As used herein, the term "acid-resistant yeast" is defined as a yeast that can maintain a biomass consumption rate (such as a sugar consumption rate) of at least 10% or a specific growth rate of at least 10%, at a pH less than a pKa value of an organic acid, when the medium contains an organic acid (particularly, lactic acid) at a concentration of at least 1M, compared to when the medium does not contain an organic acid. More specifically, the term "acid-resistant yeast" is defined as yeast that can maintain a biomass consumption rate (such as a sugar consumption rate) of at least 10% or a specific growth rate of at least 10% at a pH of 2 to 4 compared to a pH of 5 or higher.

The recombinant yeast according to the present invention can be produced by inserting the gene into a chromosome of a host yeast according to a conventional method, or by introducing a vector including the gene into the host yeast.

As the host yeast, a host cell having high DNA introduction efficiency and high expression efficiency of the introduced DNA is commonly used. Any type of yeast can be used, as long as it enables expression thereof. In one embodiment of the present invention, an acid-resistant yeast is used, but the present invention is not limited thereto, and any type of yeast may be used, as long as it can sufficiently express the target DNA.

The recombinant yeast can be prepared according to any transformation method. The term "transformation" refers to a phenomenon in which DNA is introduced into a host to enable DNA to be replicated as a factor of chromosomes or by chromosomal integration, and means a phenomenon in which genetic changes are artificially induced by introducing external DNA into a cell. General transformation methods include electroporation, lithium acetate-PEG, and the like.

In addition, in the present invention, any commonly known genetically engineering method can be used as a method of inserting genes into the chromosomes of host microorganisms. For example, there are methods using retroviral vectors, adenoviral vectors, adeno-associated virus vectors, herpes simplex viral vectors, pox virus vectors, lentiviral vectors, non-viral vectors and the like. The "vector" means a DNA product containing a DNA sequence operably linked to a suitable regulatory sequence capable of expressing the DNA in a suitable host. Vectors may be plasmids, phage particles or simply potential genomic inserts. After vectors are transformed into suitable host cells, they may be replicated or perform functions independent of the host genomes, or some thereof may be integrated with the genomes. Plasmids are currently the most commonly used forms of vectors, but linear DNA is also a commonly used form for genomic integration of yeast.

Typical plasmid vectors include (a) a replication origin to efficiently conduct replication so as to include a predetermined amount of plasmid vectors per host cell, (b) an antibiotic resistance gene or auxotrophic marker gene to screen host cells transformed with plasmid vectors, and (c) a restriction enzyme cleavage site into which a foreign DNA fragment is inserted. Even if an appropriate restriction enzyme cleavage site is not present, the vector and foreign DNA can be easily ligated using a synthetic oligonucleotide adapter or a linker according to a conventional method (Gibson assembly), and, if necessary, a method including synthesizing and using an entire desired synthesized sequence is also commonly used.

When a nucleic acid sequence is aligned with another nucleic acid sequence based on a functional relationship, it is "operably linked" thereto. This may be gene(s) and control sequence(s) linked in such a way so as to enable gene expression when a suitable molecule (e.g., a transcriptional activator protein) is linked to the control sequence(s). For example, DNA for a pre-sequence or secretory leader is operably linked to DNA for a polypeptide, when expressed as a pre-protein involved in the secretion of the polypeptide; a promoter or enhancer is operably linked to a coding sequence when it affects the transcription of the sequence; or a ribosome-binding site is operably linked to a coding sequence when it affects the transcription of the sequence; or the ribosome-binding site is operably linked to a coding sequence when positioned to facilitate translation.

Generally, the term "operably linked" means that the linked DNA sequence is in contact therewith, or that a secretory leader is in contact therewith and is present in the reading frame. However, the enhancer need not be in contact therewith. The linkage of these sequences is carried out by ligation (linkage) at convenient restriction enzyme sites. When no such site exists, a synthetic oligonucleotide adapter or a linker according to a conventional method is used.

It should be understood that not all vectors function identically in expressing the DNA sequences of the present invention. Likewise, not all hosts function identically for the same expression system. However, those skilled in the art will be able to make appropriate selections from among a variety of vectors, expression control sequences and hosts without excessive burden of experimentation and without departing from the scope of the present invention. For example, selection of a vector should be carried out in consideration of a host because the vector should be replicated therein. The number of times the vector replicates, the ability to control the number of times the vector replicates, and the expression of other proteins encoded by the corresponding vector, such as the expression of antibiotic markers, should also be considered.

In the present invention, the carbon source may include, but is not limited to, one or more selected from the group consisting of glucose, xylose, arabinose, sucrose, fructose, cellulose, galactose, glucose oligomer, and glycerol.

In the present invention, the culture may be performed under conditions such that microorganisms, for example, *E. coli*, and the like no longer act (for example, cannot produce metabolites). For example, the culture may be carried out at a pH of 1.0 to 6.5, preferably a pH of 1.0 to 6.0, and more preferably a pH of 2.6 to 4.0, but is not limited thereto.

Hereinafter, the present invention will be described in more detail with reference to examples. However, it will be obvious to those skilled in the art that these examples are

Example 1: Analysis of Lactate Consumption Gene in Genome of Acid-Resistant Yeast Strain YBC The present inventors selected strains having acid resistance through testing on various yeast strains, selected a YBC strain, which is the strain having the best acid resistance, by adding lactic acid to a medium at the beginning of the culture of yeast strains and monitoring the growth and sugar consumption rate of microorganisms, and deposited the strain under the Budapest Treaty with the Korea Research Institute of Bioscience and Biotechnology Biological Resource Center, 181, Ipsin-gil, Jeongeup-si, Jeollabuk-do, 56212, Republic of Korea, with accession number KCTC13508BP on Apr. 11, 2018.

Phylogenetic analysis showed that the YBC strain (KCTC13508BP) is a strain similar to *S. cerevisiae*, has a diploid gene, and is Crabtree-positive.

g2947 and g3864 were identified as genes annotated with CYB2, a gene encoding an enzyme that converts L-lactate, present in the genome of the YBC strain, to pyruvate using *S. cerevisiae* and bioinformatics information in full genome sequence data.

When protein domain analysis (http://smart.embl-heidelberg.de/) was performed on the CYB2 gene of *S. cerevisiae*, the CYB2 gene of *S. cerevisiae* was found to have the characteristics of a cytochrome b5 family, heme-binding domain profile and an FMN-dependent alpha-hydroxy acid dehydrogenase domain profile. When the same analysis was performed on the g2947 gene, the g2947 gene exhibits the same characteristics as the CYB2 gene of *S. Cerevisiae*, such as a cytochrome b5 family, heme-binding domain profile and an FMN-dependent alpha-hydroxy acid dehydrogenase domain profile, and the g3864 gene was found to have no heme-binding domain profile and thus it was judged that it would be difficult to impart CYB2 characteristics thereto. In addition, when analyzing the ORF near the CYB2 gene on the genome of *S. cerevisiae*, the ORFs of CMP2-IMD4-SPC2-CYB2-YML054c-A are sequentially arranged, and the same site as above exists in scaffold 41 of the YBC strain containing g2947, which indicates that there is also the possibility that ORF is present as a conserved region. Accordingly, a deletion cassette capable of removing the g2947 genes (SEQ ID NO: 1 and SEQ ID NO: 2) and proteins thereof (SEQ ID NO: 3 and SEQ ID NO: 4) was constructed.

In addition, in this embodiment, along with the cassette that only deletes (lacks) the same, a cassette capable of expressing the gene of *L. plantarum*-derived lactate dehydrogenase (LDH), which is an enzyme that generates lactate, was designed using the inherent promoter of g2947 (FIG. 1). The deletion cassette is shown in FIG. 1, and the method of selecting a corresponding restriction enzyme site or an antibiotic resistance gene and removing the antibiotic resistance gene is well known in the related art, and can be used with various modifications.

Example 2: Production of Recombinant Acid-Resistant Yeast Strain from which Lactate Consumption Gene is Removed The target acid-resistant yeast strain for removing the g2947 gene, which is expected to be the CYB2 gene, from the genome is not a wild-type strain, but is a YBC2 strain, which expresses LDH when further removing the g3002-1 gene (PDC gene) from a YBC1 strain, from which the LDH gene was introduced into the conventional wild-type strain while the main ADH (alcohol dehydrogenase) gene was removed therefrom, and produces lactic acid with high efficiency while exhibiting inhibited ethanol production ability. A YBC4 strain was produced by performing engineering to express 2 copies of the LDH gene derived from *L. plantarum* while removing the g2947 gene from the YBC2 strain (removing both allele 1 and allele 2 from the strain, which is diploid), the primers set forth in Table 1 below were produced to identify the genotype of the strain, and the genotype of the strain was identified from the genomic DNA of the strain.

The method of producing the strain is as follows:

The YBC1 strain is a strain from which the g4423 gene, which is the main ADH gene of the YBC strain, was removed and into which the LDH gene of SEQ ID NO: 7 derived from *Lactobacillus plantarum* was introduced at the g4423 position. A gene cassette, from which the ORF of each gene was removed and containing 5' and 3' UTR and antibiotic markers, was produced based on the information of g4423 and UTR thereof and used as donor DNA. For each allele of g4423, the corresponding 5' UTR is represented by SEQ ID NO: 8 and SEQ ID NO: 9, and the 3' UTR is represented by SEQ ID NO: 10 and SEQ ID NO: 11. As described above, a cloning method using a restriction enzyme and a method using Gibson assembly and gene synthesis were used for the production of donor DNA. The LDH of SEQ ID NO: 7 was synthesized at the ORF position of g4423, and was then introduced to produce donor DNA, and the donor DNA was introduced into YBC to produce a recombinant strain YBC1.

In addition, the g3002-1 gene is a gene that is present at the scaffold 72 position in the genome of the YBC strain and acts as a PDC gene. The g3002-1 gene (gene positioned at scaffold 72) was removed from the YBC1 strain, and the LDH gene of SEQ ID NO: 7 was introduced into the same to produce a recombinant strain YBC2.

In particular, UTR was used for production to replace the g3002 gene. Similar to the method of introducing LDH at the position of the g4423 gene (ADH) of YBC1 described above, the UTR of g3002-1 was used for production. However, in order to simplify the process of replacing the gene, a donor cassette was produced for one allele without consideration of allele variation, but can be produced for respective alleles. In addition, for the primers used for gene substitution, in addition to the primers used to produce the deleted strain, a pair of primers capable of identifying the UTR and LDH of g3002-1 as follows were separately used to increase the accuracy of identification of gene substitution.

g3002-1 UTR-LDH-fwd:

(SEQ ID NO: 12)

GCAGGATATCAGTTGTTTG g3002-1 UTR-LDH-rev:

(SEQ ID NO: 13)

AATACCTTGTTGAGCCATAG

The method of producing the strain is as follows:

The YBC4 strain is a strain from which the g2947 gene, which is the main CYB2 gene of the YBC2 strain, was removed and into which the LDH gene of SEQ ID NO: 7 derived from *Lactobacillus plantarum* was introduced at the position of g2947. The g2947 gene is a gene present at scaffold 41 in the genome of the YBC strain. A gene cassette from which the ORF of each gene was removed and containing 5' and 3' UTR and antibiotic markers was produced based on the information of g2947 and UTR thereof and used as donor DNA. For each allele of g2947, the corresponding 5' UTR is represented by SEQ ID NO: 5 and SEQ ID NO: 6, and the 3' UTR is represented by SEQ ID NO: 14 and SEQ ID NO: 15. As described above, a cloning method using a restriction enzyme and a method using Gibson assembly and gene synthesis were used for the production of donor DNA.

In order to simplify the process of replacing the gene, a donor cassette was produced for one allele without consideration of allele variation, but can be produced for respective alleles. In addition, for the primers used for gene substitution, in addition to the primers used to produce the deletion strain, a pair of primers capable of identifying the UTR and LDH of g2947 set forth in the following Table 1 were separately used to increase the accuracy of identification of gene substitution.

TABLE 1

Primer set for identifying introduction of g2947

| Names | Corresponding Sequences |
|---|---|
| Primer for identifying introduction of G2947 ORF | CTAGTTGTGGTTCCTTGTAT (SEQ ID NO: 16)<br>GAAAATAAATCCGATGGTGC (SEQ ID NO: 17) |
| 2$^{nd}$ primer set for identifying introduction of G2947 ORF | TGTTTGACTGTTCGATATGG (SEQ ID NO: 18)<br>GAAAATAAATCCGATGGTGC (SEQ ID NO: 19) |
| Primer for identifying introduction of G2947 UTR | TGTTTGACTGTTCGATATGG (SEQ ID NO: 20)<br>GAAGATTGAAAGGGTCAGT (SEQ ID NO: 21) |
| Primer for identifying introduction of G2947 LDH | GACTAATCACCCAACTCTCA (SEQ ID NO: 22)<br>ATCGCCGAGGTACTAGAG (SEQ ID NO: 23) |

The genotype of the produced recombinant strain is as follows:

YBC2: Δg4423::ldh/Δg3002-1::ldh

YBC4: Δg4423::ldh/Δg3002-1::ldh/Δg2947::ldh

Example 3: Determination of Effects of Improved Lactic Acid Production and Inhibited Ethanol Production in Recombinant YBC Strain Obtained by Deleting CYB2 Gene from YBC2 Strain and Introducing LDH into YBC2 Strain The recombinant strains YBC2 and YBC4 produced in Example 2 were cultured in a 100 ml flask at an inoculation OD of 0.5, in, as a medium, YP medium (20 g/L peptone, 10 g/L yeast extract) supplemented with 6% glucose at 30° C. and 175 rpm for 4 hours, and then cultured at 125 rpm.

TABLE 2

Culture results of YBC2 and YBC4

| | Yield (g/g) | | | | | | | |
|---|---|---|---|---|---|---|---|---|
| | Lactic acid | Ethanol | Glycerol | Acetic acid | Pyruvic acid | Succinic acid | Productivity (g/L/hr) | pH |
| YBC2 | 0.66 | 0.083 | 0.03 | 0.002 | 0.002 | 0.01 | 1.31 | 2.74 |
| YBC4 | 0.84 | 0.004 | 0.03 | 0 | 0.002 | 0.005 | 1.55 | 2.59 |

Figure 2:
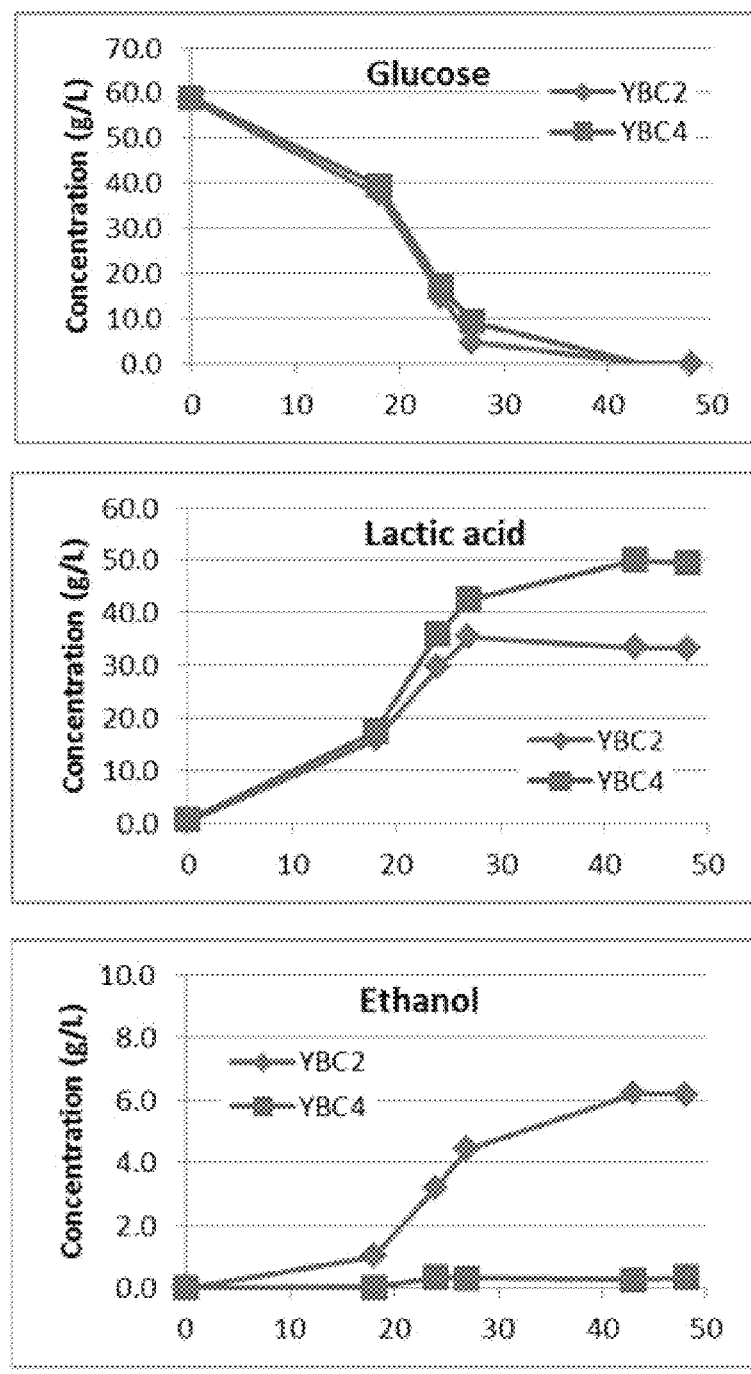
FIG. 2 shows the results of culture of YBC2 and YBC4 strains.

As a result, as can be seen from Table 2 and FIG. 2, the YBC4 strain significantly increased the yield of lactic acid fermentation compared to the YBC2 strain. On the other hand, the YBC4 strain decreased the ethanol fermentation yield by more than 90% compared to the YBC2 strain, which means that all carbon flux was converted from ethanol to lactic acid, and thus the yield of lactic acid increased up to 84% of a theoretical value therefor. In general, in neutral fermentation, the lactic acid yield may be as high as about 90% to about 94%, excluding carbon consumed for strain growth. However, in the acid-resistant strain, there is an undissociated form of lactic acid flux that diffuses through the cell membrane from the outside, and transport to the outside through a transporter is required in order to reduce stress caused by internally produced lactic acid and externally introduced lactic acid. In such transport, when the external lactic acid concentration is low, transport in the form of a simple permease is possible, and in this case, consumption of ATP is not required, but when the concentration of external lactic acid increases, energy is required in order to transport lactic acid against the concentration gradient, and in this process, ATP is consumed (Antonius J. A. van Maris et al., *Metabolic Engineering* 6: 245, 2004). The consumption of ATP inevitably causes additional carbon loss. Thus, only the present invention shows the result of obtaining a yield of 0.8 or more, while producing lactic acid at a high concentration of 50 g/L at a pH of 3 or less, using no neutralizing agent or using a minimum amount of a neutralizing agent.

As a result of determining whether or not lactic acid is consumed when there is no glucose after the end of culture for lactic acid consumption, which is the original function of g2947, it was found that lactic acid slowly disappeared in the YBC2 strain, similar to the previous results, but that no decrease in lactic acid was observed in the YBC4 strain from which the g2947 gene was deleted, which means that the g2947 gene was a CYB2 gene. The most outstanding performance of the YBC4 strain is to completely prevent ethanol production along with an increase in the yield of lactic acid. With regard to the effects of removing the CYB2 gene, it has been reported that the produced lactic acid was not consumed even if the glucose concentration was lowered at the end of fermentation, that there was an increase in the yield of some of the lactic acid, and that the increase in yield was also not visible at a pH above pKa, but the yield increased from 19.3% to 28.6% only at pH 3.5 (Aki Ookubo et al., *Biosci. Biotechnol. Biochem.*, 72:3063, 2008). However, the results of this Example showed that the strain (YBC2), which already showed a high lactic acid production yield along with inhibition of consumption of lactate, further dramatically increased a lactic acid yield and completely blocked the production of ethanol. The reason for this may be explained as follows. First, the CYB2 gene can supply additional pyruvate while converting lactate to pyruvate in the mitochondrial membrane. This pyruvate can be converted to ethanol, and thus the production of ethanol therefrom can be suppressed by removing the CYB2 gene. In particular, it is considered that a small amount of ethanol is produced by auxiliary ADHs including ADH3 and auxiliary PDCs, which play a role in mitochondria, since only the main ADH and the main PDC are removed in the genotype of this strain. The second reason for this is that the LDH inside the YBC bacteria is enhanced due to the additional expression of LDH introduced at the position of CYB2, and thus the pathway from pyruvate to lactate is more selective in the state in which the pathway from pyruvate to ethanol is already weakened, thus decreasing the yield of ethanol. It is considered that the production of ethanol can be completely prevented through a combination of the two effects.

Example 4: Determination of Effects of Improving Lactic Acid Production and Inhibiting Ethanol Production in Recombinant YBC Strain Obtained by Deleting CYB2 Gene from Wild-Type YBC Strain and Introducing LDH into Strain The results of Example 3 showed that the lactic acid production ability increased and the ethanol production ability decreased through the removal of the g2947 gene and expression of LDH. However, the above results were caused by the combined effect due to removal of genes other than the g2947 gene, since the YBC2 strain used as the parent strain was a strain from which ADC and PDC genes were deleted.

Accordingly, a strain that expresses LDH when removing only the g2947 gene from the wild-type YBC strain was produced, and lactic acid production ability and ethanol production inhibition ability thereof were determined. The strain was produced by the method shown in Example 2 using cassettes used for production of the recombinant strain and primers used for identifying the genotypes shown in FIG. 1 and Table 1.

The strain resulting from removal of the g2947 gene from the YBC strain and insertion of LDH therein was designated as "YBC_a", and the genotype thereof is as follows.

YBC_a: Δg2947::ldh

The recombinant strain was cultured in a 50 ml culture volume in a 500 ml flask at an inoculation OD of about 0.5 in, as a medium, a mYP medium (5 g/L peptone, 4 g/L yeast extract, 5 g/L KH$_2$PO$_4$, 2 g/L MgSO$_4$.7H$_2$O, 0.15 g/L uracil) supplemented with 6% glucose at 30° C. and 125 rpm.

In addition, in order to further observe the induction effect by lactic acid, lactic acid was injected at an initial concentration of 11.5 g/L into the culture solution at the beginning of the culture and then cultured.

TABLE 3

Lactic acid and ethanol yield of YBC a strain

| | Yield (g/g) | |
|---|---|---|
| | Lactic acid | Ethanol |
| Wild type | 0 | 0.44 |
| YBC_a | 0.02 | 0.37 |
| YBC_a | 0.09 | 0.35 |
| Initial lactic acid addition | | |

As shown in Table 3, the ethanol yield of the YBC_a strain was lower than a general ethanol yield, that is, 0.43 to 0.45 g/g, of the wild-type strain, and thus the effect of reducing the ethanol yield through removal of the CYB2 gene was proved. Interestingly, it can also be seen that when only the LDH gene is introduced at the position of the CYB2 gene, hardly any lactic acid can be produced. This means that the promoter of CYB2 cannot be expressed without lactic acid in the presence of glucose, which is a general fermentation condition, and shows that there is an effect of reducing the amount of ethanol that is produced even though lactic acid was not produced. When lactic acid is added to the culture medium at the beginning of the culture to determine the induction effect of the CYB2 gene, the lactic acid is mass-transferred or actively transferred into the cell, so the CYB2 promoter reacts with lactic acid in the cell to express the LDH gene substituted at the position of CYB2, thereby increasing the yield of lactic acid and decreasing the yield of additional ethanol.

This means that the CYB2 promoter can self-induce expression of the LDH gene in the lactic-acid-producing strain, which is a promoter that is different from promoters that are strongly expressed at the beginning of culture under glucose-rich conditions and strongly expressed in general glycolysis conditions, and can continuously maintain the ability of cells to produce lactic acid by expressing the LDH gene at the end of culture, and is thus highly useful for the production of highly efficient lactic-acid-producing strains. The promoter region of the g2947 gene is represented by SEQ ID NO: 5 and SEQ ID NO: 6.

These CYB2 removal effects of the present invention are improved compared to the prior art, and the previous study reported that the yield of lactic acid slightly increased only at a low pH, but there is no mention of reduced ethanol production (Aki Ookubo et al., *Biosci. Biotechnol. Biochem.*, 72:3063, 2008). Natureworks' patents, WO 2007117282 and U.S. Pat. No. 8,137,953B, disclose the production of a strain producing lactic acid from *I. orientalis* and the development of a strain through removal of CYB2 from this strain. In this case, the strain that produced lactate at a rate of 0.35 g/L/hr, a concentration of 56 g/L, and a yield of 69% at pH 3, before removal of CYB2, produced lactate at a rate of 0.43 g/L/hr, a concentration of 66 g/L and a yield of 67%, after CYB2 removal. This result showed that the concentration of the produced lactate increased, but the yield decreased thereof, and glycerol was also increased as a by-product. In addition, U.S. Pat. No. 9,353,388B granted to the Samsung Advanced Institute of Technology discloses that a production of a lactic-acid-producing microorganism, and also discloses a microorganism from which the CYB2 gene is removed (SP1002 performance evaluation of Table 3 in the corresponding patent), or a microorganism expressing the LDH gene when the CYB2 gene is removed (see the effects of overexpression of Jen1 and Ady2 on sp1003 and sp1002 of Table 4 of the corresponding patent). At this time, the effect of increasing the concentration of produced lactic acid was observed. However, the above patent does not disclose an effect of completely inhibiting ethanol production. Thus, it is deemed that the effects caused by the removal of the CYB2 gene and expression of the LDH gene in the YBC strain in the present invention are excellent.

Example 5: Production of Strain Expressing LDH when Removing CYB2 Gene from YBC1 Strain and Evaluation of Performance Thereof The result shows that YBC4 can improve lactic acid production and inhibit ethanol production by removing the g2947 gene from a strain, obtained by removing the main ADH (g4423) and the main PDC (g3002-1) from the YBC strain, and by introducing the LDH gene into the strain. A recombinant strain was produced to determine the combined effect of only the main ADH gene and the g2947 gene, and the fermentation ability thereof was determined.

The recombinant strain was produced by removing ADH (g4423) and g2947 and introducing the LDH gene into the strain in the same manner as in Example 2 using the cassette and primer set used in Example 2.

The produced recombinant strain was designated as YBC_b, and the genotype thereof is as follows.

YBC_b: $\Delta$g4423::ldh/$\Delta$g2947::ldh

The recombinant strain was cultured in a 60 ml culture volume in a 500 ml flask at an inoculation OD of about 0.5 in, as a medium, a mYP medium (5 g/L peptone, 4 g/L yeast extract, 5 g/L $KH_2PO_4$, 2 g/L $MgSO.7H_2O$, 0.15 g/L uracil) supplemented with 10% glucose at 30° C. and 125 rpm. In this culture, the initial glucose concentration was high, the pH decrease caused by the lactic acid that was produced was large, and growth inhibition was expected. Thus, 1 ml of a 40% $CaCO_3$ solution was injected twice to adjust the final pH to 3. In addition, for comparison, the YBC4 strain was cultured under the same conditions as above.

TABLE 4

Comparison of yields of lactic acid and ethanol of YBC_b strain

| | Yield (g/g) | | |
|---|---|---|---|
| | Lactic acid | Ethanol | Glycerol |
| YBC_b | 0.73 | 0.023 | 0.06 |
| YBC1 | 0.59 | 0.093 | 0.045 |
| YBC4 | 0.81 | 0.002 | 0.04 |

As a result, as can be seen from Table 4, when compared with the YBC4 strain blocking the production of ethanol, the YBC_b strain produced ethanol and exhibited a lower lactic acid yield, which is considered to be due to the fact that the main PDC (g3002-1) of the YBC_b strain is active, so LDH and PDC compete with each other in pyruvate, and ethanol is produced therefrom. However, taking into consideration the fact that the ethanol yield of the YBC1 ($\Delta$g4423::ldh) strain is 0.07 to 0.1 g/g, the ethanol yield of the YBC_b strain is significantly lower (0.023 g/g). This further demonstrates the effects caused by the deletion of the g2947 gene.

Example 6: Production of Strains Obtained by Removing Only CYB2 Gene from YBC2 Strain and Performance Evaluation Thereof The result shows that YBC4 can improve lactic acid production and inhibit ethanol production by removing the g2947 gene from a strain obtained by removing the main ADH (g4423) and the main PDC (g3002-1) from the YBC strain, and introducing the LDH gene into the strain. A recombinant strain was produced by removing only the g2947 gene from the YBC2 strain to determine an effect other than expression of LDH, and the fermentation ability thereof was determined.

The recombinant strain was produced in the same manner as in Example 2 using the cassette and primer set used in Example 2. Since there is no LDH expression, the "primer for identifying the introduction of G2947 LDH" in Table 1 was not used.

The produced recombinant strain was designated as YBC_c, and the genotype thereof is as follows.

YBC_c: $\Delta$g4423::ldh/$\Delta$g3002-1::ldh/$\Delta$2947

The recombinant strain was cultured in a 60 ml culture volume in a 500 ml flask at an OD of about 0.5 in, as a medium, a mYP medium (5 g/L peptone, 4 g/L yeast extract, 5 g/L $KH_2PO_4$, 2 g/L $MgSO_4.7H_2O$, 0.15 g/L uracil) supplemented with 10% glucose at 30° C. and 150 rpm. In this culture, the initial glucose concentration was high, the pH decrease caused by the lactic acid that was produced was large, and growth inhibition was expected. Thus, 1 ml of a 40% $CaCO_3$ solution was injected twice to adjust the final pH to 3. In addition, for comparison, the YBC4 strain was cultured under the same conditions as above.

TABLE 5

Comparison of yields of lactic acid and ethanol of YBC_c strain

| | Yield (g/g) | | |
|---|---|---|---|
| | Lactic acid | Ethanol | Glycerol |
| YBC_c | 0.73 | 0.044 | 0.05 |
| YBC4 | 0.81 | 0.002 | 0.04 |

As a result, as can be seen from Table 5, when compared with the YBC4 strain, the YBC_c strain had the same effects on the yield of ethanol and lactic acid due to non-expression of LDH, and when compared with the YBC2 in Table 1, the YBC_c strain still exhibited the effect of removal of the g2947 gene.

Example 7: Confirmation of Productivity Increase Effect According to Initial Inoculation Concentration of YBC4 Strain In general, when the initial inoculation concentration increases during fermentation, an increase in yield and productivity can be expected. The effect was determined by applying the same method to the YBC4 strain.

In the same seed culture of YBC4, the inoculation OD was changed from 0.5 to 2 by mixing with distilled water. The recombinant strain was cultured in a 55.5 ml culture volume in a 500 ml flask, as a medium, a mYP medium (5 g/L peptone, 4 g/L yeast extract, 5 g/L $KH_2PO_4$, 2 g/L $MgSO_4.7H_2O$, 0.15 g/L uracil) supplemented with 8.7% glucose at 30° C. and 150 rpm.

TABLE 6

Comparison in yield and productivity according to initial inoculation concentration of YBC4 strain

| | Yield (g/g) | | | Productivity | |
| --- | --- | --- | --- | --- | --- |
| | Lactic acid | Ethanol | Glycerol | (g/L/hr) | pH |
| OD 0.5 | 0.81 | 0.009 | 0.04 | 1.83 | 2.6 |
| OD 1 | 0.81 | 0.012 | 0.04 | 2.06 | 2.6 |
| OD 1.5 | 0.81 | 0.008 | 0.04 | 2.09 | 2.6 |
| OD 2 | 0.80 | 0.007 | 0.04 | 2.13 | 2.6 |

As a result, as can be seen from Table 6, productivity increased with an increase in the initial inoculation OD value, but there was little change in the yield. This means that the proportion of carbon that was consumed to reach the final OD of 10 does not vary significantly depending on the difference in the initial OD.

Table 7 shows the culture results compared with the two best previously reported results of lactic acid production by acid-resistant yeasts at a pH of 3 or less.

TABLE 7

Comparison in lactic acid production yield and productivity between YBC4 strain and acid-resistant yeast of prior patent

| | Lactic acid yield (g/g) | Productivity (g/L/hr) | Lactic acid concentration (g/L) | pH |
| --- | --- | --- | --- | --- |
| US 2009/0053782 A1 | 0.80 | 1.68 | 70 | 3 |
| WO 2005/052174 A2 | 0.79 | 0.73 | 53.8 | 2.75 |
| Example 7 | 0.81 | 2.1 | 70 | 2.6 |

(US 2009/0053782 A is based on performance at concentration, and WO 2005/052174A is based on yield per amount injected)

As can be seen from Table 7, the YBC4 strain has the highest lactic acid productivity.

Example 8: Evaluation of Fermentation Performance of YBC4 Strain

The YBC4 strain was cultured in a bioreactor rather than a flask culture to determine the lactic acid fermentation performance thereof.

Figure 3:
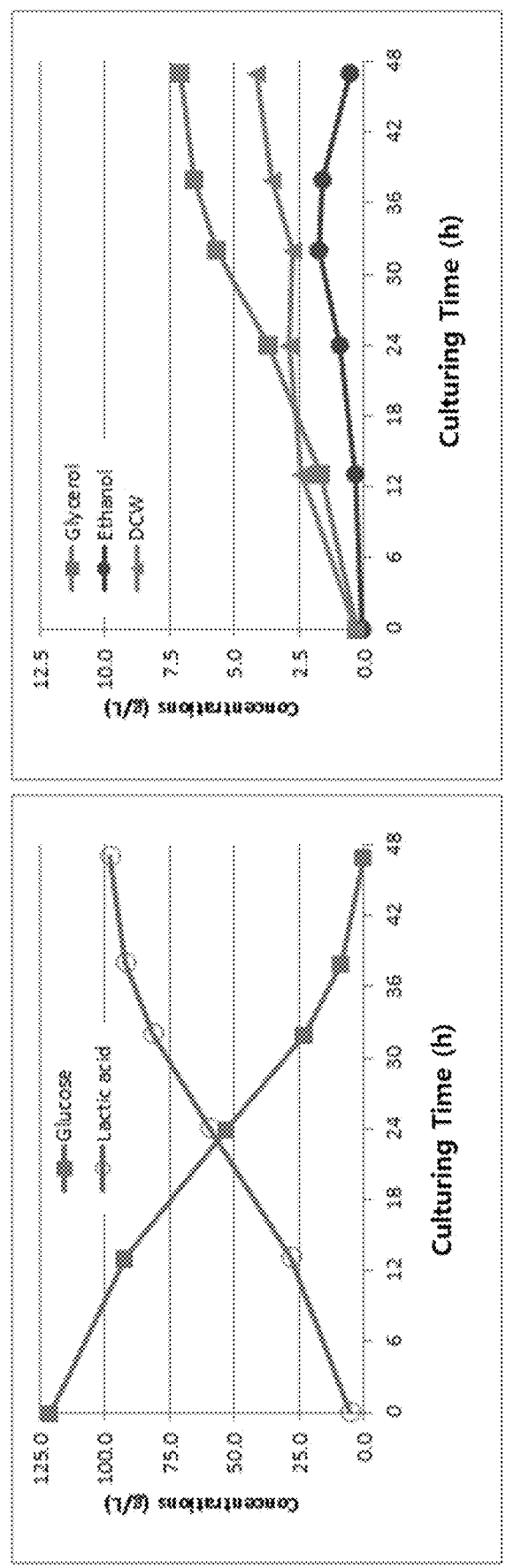
FIG. 3 shows the fermentation profile of the YBC4 strain.

The strain was started to be cultured at an OD of 1 in, as a medium, a mYP medium (5 g/L peptone, 4 g/L yeast extract, 5 g/L $KH_2PO_4$, 2 g/L $MgSO_4.7H_2O$, 0.15 g/L uracil) supplemented with 12% glucose. A $CaCO_3$ solution was intermittently injected to maintain a pH of 3. The strain was cultured by injecting into a 2.5 L culture solution at 30° C. and at 450 rpm, along with 0.1 vvm of air. As a result, as can be seen from FIG. 3, the YBC4 strain consumed all glucose within a short time in the bioreactor to produce lactic acid, and the lactic acid yield was 0.8 (g/g) at the final pH of 3.3, the productivity was 2.0 g/L/hr, and the produced lactic acid concentration was 98.1 g/L. In addition, it is expected that further performance improvement is possible depending on initial OD and culture conditions in the future.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

What is claimed is:

1. A recombinant strain having lactic-acid-producing ability, in which a gene comprising the nucleotide sequence of SEQ ID NO: 1 or SEQ ID NO: 2 encoding an enzyme converting lactate to pyruvate is deleted or attenuated from an acid-resistant yeast strain KCTC13508BP;
   a gene encoding an alcohol dehydrogenase and/or a gene encoding a pyruvate decarboxylase is deleted; and
   a gene comprising the nucleotide sequence of SEQ ID NO: 7 encoding a lactate dehydrogenase is introduced into the acid-resistant yeast strain.

2. The recombinant strain according to claim 1, wherein the gene having the nucleotide sequence of SEQ ID NO: 7 encoding the lactate dehydrogenase is introduced by substitution with the gene having the nucleotide sequence of SEQ ID NO: 1 or SEQ ID NO: 2 encoding an enzyme converting lactate to pyruvate and is regulated by a promoter of the gene encoding an enzyme converting lactate to pyruvate.

3. A method of producing lactic acid comprising:
   (a) culturing the recombinant strain according to of claim 1 to produce lactic acid; and
   (b) obtaining the produced lactic acid.

* * * * *

SEQUENCE LISTING

```
<160> NUMBER OF SEQ ID NOS: 23

<210> SEQ ID NO 1
<211> LENGTH: 1851
<212> TYPE: DNA
<213> ORGANISM: Artificial Sequence
<220> FEATURE:
<223> OTHER INFORMATION: g2947 allele1_ORF

<400> SEQUENCE: 1
atgcaagcaa tttcaaaaaa ttcaacattt ttacgtaatt gtaaaaattt gaaatttatt     60
tcaaagaaca ttaataatag gaagttatct tcttcatcta taactttatc acaattacaa    120
tcaattaaaa ctaataccaa ttataagaat tattcttcca aaaatttacg taattcatta    180
attttattat cgtctgtatc atttttagct tattacgcta atgatcaatt acaacataat    240
actaattcat taatatctaa tgataatggt aagaatccag ctgctaataa gaaaccaatc    300
tctccagcag aagttgctaa acataacaaa ccagatgatt gttgggtagt tattgacggt    360
tacgtttacg atgtctcttt ctttattcca aatcatccag gtggtgaaga tgtcattaga    420
gctaatgcag gtaaggatgt taccgctatc ttcatgccat tacatgctaa gggtacccett    480 gaaaagaata ttccaattga aaatcaatta ggtccattaa gtaaaccaat gcctaaaaaa    540
ttagtttgtc caccttatgc tcctggtgag acaccttatg aaattatgac taaacaaaaa    600
ttaagagata atatgccacc attaggcaca atttaaatc tttatgattt tgagagatta    660
gcttcaaaaa ttttaactaa tcaagcttgg gcttattatt cttctggtgc agatgatgaa    720
```

```
attacatata gagaaaacca taacgcttat catagaatct ttttcaaacc acatatttta      780
gtcgatgtta aggatgtcga tttgaagact actatgttag gtaataagac cgatgttcca      840
ttctatgtta gtgctactgc tttatgtaaa ttaggtaatc cagaaggtgg tgaagttgat      900
atcgctaaag gttgtggttc aacttcttat atggttcctc aaatgatttc tactttagct      960
tcttgttcat tagatgaagt cgcccagggg aaagctaacg ataaacaatt acaatggttt     1020
caattatatg ttaattccga tagaaagatt actagaaatt taattaaaca tgctgaagat     1080
ttaggtatga aggctatctt cgtcacagtt gatgctcctt ctttaggtaa tagagaaaag     1140
gatcaaaaga ttaaatttac tactcaaggt tctgagggtc aaagattttt acaaaagaaa     1200
ggtgattcct ccaatgctgc tgctgaagca agaagaaaag aaaataaatc cgatggtgcc     1260
tctaaagctt tatctaaatt tatcgatcct tctttgtcct gggaagatat cgcaaagatg     1320
agaaaattga ctaaattacc aatcgttatt aagggtgttc aaagagctga agatgctgta     1380
agagcagctc aaatgggttg tcaaggtgtt gttctttcaa atcatggtgg tagacaatta     1440
gatttctcaa gagccccaat tgaagttctt gcagagacta tgccaatttt gaaacatcat     1500
ggtctagata agaatttcga tgtctttgtc gatggtggta ttcgccgtgg tactgatatc     1560
ttaaaggcat tgtgtcttgg tgctacaggt gttggtttag gtagaccttt cttatatgct     1620
aattcttgtt atggtagaga tggtgttgct catgctattg atatcattac caaagaatta     1680
gaaatgtcta tgagattatt aggtgttagc aaaattgagg atttgaatcc aggtttctta     1740
gatttacaat ctttacatgc cagatctgtt cttgttgcta aggatgcatt atatgaaaat     1800
tcatacaagg aaccacaact agctaaattc ttaattgacg acgatgatta g              1851

<210> SEQ ID NO 2
<211> LENGTH: 1827
<212> TYPE: DNA
<213> ORGANISM: Artificial Sequence
<220> FEATURE:
<223> OTHER INFORMATION: g2947 allele 2 ORF

<400> SEQUENCE: 2
atgcaagcaa ttaattttaa aaatttgaaa tttattcaa agaacattaa taataggaag        60
ttatcttctt catctataac tttatcacaa ttacaatcaa ttaaaacaaa taccaattac      120
aagaattatt cttccaaaaa tttacgtaat tcattaattt tattatcttc tgtatcattt      180
ttagcttatt acgctaatga tcagttacaa cagaatacta attcattaat atctaatgaa      240
aatggtaaga atccagctgc taataagaaa ccaatctctc cagcagaagt tgctaaacat      300
aacaaaccag atgattgttg ggtagttatt gacggttacg tttacgatgt ctctttcttt      360
attccaaatc atccaggtgg tgaagatgtc attagagcta atgcaggtaa ggatgttacc      420
gctatcttca tgccattgca tgctaagggt acccttgaaa gaatattcc aattgaaaat      480 caattaggtc cattaagtaa accaatgcct aaaaaattag tttgtccacc ttatgctcct      540
ggtgagacac cttatgaaat tatgactaaa caaaaattga gagataatat gccaccatta      600
ggtacaattt taaatcttta tgattttgaa agattagctt caaaaatttt aactaatcaa      660
gcttgggctt attattcttc tggtgcagat gatgaaatta catatagaga aaaccataac      720
gcttatcata gaatcttttt caaaccacat attttagtcg atgttaagga tgtcgatttg      780
aagactacta tgttaggtaa taagaccgat gttccattct atgttagtgc tactgcttta      840
tgtaaattag gtaatccaga aggtggtgaa gttgatatcg ctaaaggttg tggttcaact      900
```

-continued

```
tcttatatgg ttcctcaaat gatttctaca ttagcttctt gttcattaga tgaagtcgcc    960
caagggaaaa ctaacgataa acaattacaa tggtttcaat tatatgttaa ttccgataga   1020
aagattacta gaaatttaat taaacatgct gaagatttag gtatgaaggc tatcttcgtc   1080
acagttgatg ctccttcttt aggtaataga gaaaaggatc aaaagattaa atttactact   1140
caaggttctg agggtccaaa gattttacaa agaaaggtg attcctccaa tgctgctgct    1200
gaagcaaaga agaaagaaaa taatccgat ggtgcctcta agctttatc taaatttatc     1260 gatccttctt tgtcttggga agatatcgca aagatgagaa aattgactaa attaccaatc   1320
gttattaagg gtgttcaaag agctgaagat gctgtcagag cagctcaaat gggttgtcaa   1380
ggtgttgttc tttcaaatca tggtggtaga caattagatt tctcaagagc cccaattgaa   1440
gttcttgcag agactatgcc aattttgaaa catcatggtc tagataagaa tttcgatgtc   1500
tttgtcgatg gtggtattcg tcgtggtact gatatcttaa aggcattatg tcttggtgct   1560
acaggtgttg gttaggtag acctttctta tatgctaatt cttgttatgg tagagatggt    1620
gttgctcatg ctattgatat cattaccaaa gaattagaaa tgtctatgag actattaggt   1680
gttagtaaaa ttgaggattt gaatccaggt ttcttagatt tacaatcttt acatgccaga   1740
tctgttcttg ttgctaagga tgcattatat gaaaattcat acaaggaacc acaactagct   1800
aaattcttaa ttgacgacga tgattag                                       1827
```

<210> SEQ ID NO 3
<211> LENGTH: 616
<212> TYPE: PRT
<213> ORGANISM: Artificial Sequence
<220> FEATURE:
<223> OTHER INFORMATION: g2947 allele 1

<400> SEQUENCE: 3

```
Met Gln Ala Ile Ser Lys Asn Ser Thr Phe Leu Arg Asn Cys Lys Asn
1               5                   10                  15

Leu Lys Phe Ile Ser Lys Asn Ile Asn Asn Arg Lys Leu Ser Ser Ser
            20                  25                  30

Ser Ile Thr Leu Ser Gln Leu Gln Ser Ile Lys Thr Asn Thr Asn Tyr
        35                  40                  45

Lys Asn Tyr Ser Ser Lys Asn Leu Arg Asn Ser Leu Ile Leu Leu Ser
    50                  55                  60

Ser Val Ser Phe Leu Ala Tyr Tyr Ala Asn Asp Gln Leu Gln His Asn
65                  70                  75                  80

Thr Asn Ser Leu Ile Ser Asn Asp Asn Gly Lys Asn Pro Ala Ala Asn
                85                  90                  95

Lys Lys Pro Ile Ser Pro Ala Glu Val Ala Lys His Asn Lys Pro Asp
            100                 105                 110

Asp Cys Trp Val Val Ile Asp Gly Tyr Val Tyr Asp Val Ser Phe Phe
        115                 120                 125

Ile Pro Asn His Pro Gly Gly Glu Asp Val Ile Arg Ala Asn Ala Gly
    130                 135                 140

Lys Asp Val Thr Ala Ile Phe Met Pro Leu His Ala Lys Gly Thr Leu
145                 150                 155                 160

Glu Lys Asn Ile Pro Ile Glu Asn Gln Leu Gly Pro Leu Ser Lys Pro
                165                 170                 175

Met Pro Lys Lys Leu Val Cys Pro Pro Tyr Ala Pro Gly Glu Thr Pro
            180                 185                 190

Tyr Glu Ile Met Thr Lys Gln Lys Leu Arg Asp Asn Met Pro Pro Leu
```

```
            195                 200                 205
Gly Thr Ile Leu Asn Leu Tyr Asp Phe Glu Arg Leu Ala Ser Lys Ile
        210                 215                 220

Leu Thr Asn Gln Ala Trp Ala Tyr Tyr Ser Ser Gly Ala Asp Asp Glu
225                 230                 235                 240

Ile Thr Tyr Arg Glu Asn His Asn Ala Tyr His Arg Ile Phe Phe Lys
                245                 250                 255

Pro His Ile Leu Val Asp Val Lys Asp Val Asp Leu Lys Thr Thr Met
            260                 265                 270

Leu Gly Asn Lys Thr Asp Val Pro Phe Tyr Val Ser Ala Thr Ala Leu
        275                 280                 285

Cys Lys Leu Gly Asn Pro Glu Gly Glu Val Asp Ile Ala Lys Gly
290                 295                 300

Cys Gly Ser Thr Ser Tyr Met Val Pro Gln Met Ile Ser Thr Leu Ala
305                 310                 315                 320

Ser Cys Ser Leu Asp Glu Val Ala Gln Gly Lys Ala Asn Asp Lys Gln
                325                 330                 335

Leu Gln Trp Phe Gln Leu Tyr Val Asn Ser Asp Arg Lys Ile Thr Arg
            340                 345                 350

Asn Leu Ile Lys His Ala Glu Asp Leu Gly Met Lys Ala Ile Phe Val
        355                 360                 365

Thr Val Asp Ala Pro Ser Leu Gly Asn Arg Gly Lys Asp Gln Lys Ile
370                 375                 380

Lys Phe Thr Thr Gln Gly Ser Glu Gly Pro Lys Ile Leu Gln Lys Lys
385                 390                 395                 400

Gly Asp Ser Ser Asn Ala Ala Ala Glu Ala Lys Lys Glu Asn Lys
                405                 410                 415

Ser Asp Gly Ala Ser Lys Ala Leu Ser Lys Phe Ile Asp Pro Ser Leu
            420                 425                 430

Ser Trp Glu Asp Ile Ala Lys Met Arg Lys Leu Thr Lys Leu Pro Ile
        435                 440                 445

Val Ile Lys Gly Val Gln Arg Ala Glu Asp Ala Val Arg Ala Ala Gln
450                 455                 460

Met Gly Cys Gln Gly Val Val Leu Ser Asn His Gly Gly Arg Gln Leu
465                 470                 475                 480

Asp Phe Ser Arg Ala Pro Ile Glu Val Leu Ala Glu Thr Met Pro Ile
                485                 490                 495

Leu Lys His His Gly Leu Asp Lys Asn Phe Asp Val Phe Val Asp Gly
            500                 505                 510

Gly Ile Arg Arg Gly Thr Asp Ile Leu Lys Ala Leu Cys Leu Gly Ala
        515                 520                 525

Thr Gly Val Gly Leu Gly Arg Pro Phe Leu Tyr Ala Asn Ser Cys Tyr
530                 535                 540

Gly Arg Asp Gly Val Ala His Ala Ile Asp Ile Thr Lys Glu Leu
545                 550                 555                 560

Glu Met Ser Met Arg Leu Leu Gly Val Ser Lys Ile Glu Asp Leu Asn
                565                 570                 575

Pro Gly Phe Leu Asp Leu Gln Ser Leu His Ala Arg Ser Val Leu Val
            580                 585                 590

Ala Lys Asp Ala Leu Tyr Glu Asn Ser Tyr Lys Glu Pro Gln Leu Ala
        595                 600                 605

Lys Phe Leu Ile Asp Asp Asp
    610                 615
```

```
<210> SEQ ID NO 4
<211> LENGTH: 608
<212> TYPE: PRT
<213> ORGANISM: Artificial Sequence
<220> FEATURE:
<223> OTHER INFORMATION: g2947 allele 2

<400> SEQUENCE: 4
```

Met Gln Ala Ile Asn Phe Lys Asn Leu Lys Phe Ile Ser Lys Asn Ile
1               5                   10                  15

Asn Asn Arg Lys Leu Ser Ser Ser Ile Thr Leu Ser Gln Leu Gln
            20                  25                  30

Ser Ile Lys Thr Asn Thr Asn Tyr Lys Asn Tyr Ser Ser Lys Asn Leu
                35                  40                  45

Arg Asn Ser Leu Ile Leu Leu Ser Ser Val Ser Phe Leu Ala Tyr Tyr
    50                  55                  60

Ala Asn Asp Gln Leu Gln Gln Asn Thr Asn Ser Leu Ile Ser Asn Glu
65                  70                  75                  80

Asn Gly Lys Asn Pro Ala Ala Asn Lys Lys Pro Ile Ser Pro Ala Glu
                85                  90                  95

Val Ala Lys His Asn Lys Pro Asp Asp Cys Trp Val Val Ile Asp Gly
                100                 105                 110

Tyr Val Tyr Asp Val Ser Phe Phe Ile Pro Asn His Pro Gly Gly Glu
            115                 120                 125

Asp Val Ile Arg Ala Asn Ala Gly Lys Asp Val Thr Ala Ile Phe Met
    130                 135                 140

Pro Leu His Ala Lys Gly Thr Leu Glu Lys Asn Ile Pro Ile Glu Asn
145                 150                 155                 160

Gln Leu Gly Pro Leu Ser Lys Pro Met Pro Lys Lys Leu Val Cys Pro
                165                 170                 175

Pro Tyr Ala Pro Gly Glu Thr Pro Tyr Glu Ile Met Thr Lys Gln Lys
            180                 185                 190

Leu Arg Asp Asn Met Pro Pro Leu Gly Thr Ile Leu Asn Leu Tyr Asp
        195                 200                 205

Phe Glu Arg Leu Ala Ser Lys Ile Leu Thr Asn Gln Ala Trp Ala Tyr
    210                 215                 220

Tyr Ser Ser Gly Ala Asp Asp Glu Ile Thr Tyr Arg Glu Asn His Asn
225                 230                 235                 240

Ala Tyr His Arg Ile Phe Phe Lys Pro His Ile Leu Val Asp Val Lys
                245                 250                 255

Asp Val Asp Leu Lys Thr Thr Met Leu Gly Asn Lys Thr Asp Val Pro
            260                 265                 270

Phe Tyr Val Ser Ala Thr Ala Leu Cys Lys Leu Gly Asn Pro Glu Gly
        275                 280                 285

Gly Glu Val Asp Ile Ala Lys Gly Cys Gly Ser Thr Ser Tyr Met Val
    290                 295                 300

Pro Gln Met Ile Ser Thr Leu Ala Ser Cys Ser Leu Asp Glu Val Ala
305                 310                 315                 320

Gln Gly Lys Thr Asn Asp Lys Gln Leu Gln Trp Phe Gln Leu Tyr Val
                325                 330                 335

Asn Ser Asp Arg Lys Ile Thr Arg Asn Leu Ile Lys His Ala Glu Asp
            340                 345                 350

Leu Gly Met Lys Ala Ile Phe Val Thr Val Asp Ala Pro Ser Leu Gly
        355                 360                 365

Asn Arg Glu Lys Asp Gln Lys Ile Lys Phe Thr Thr Gln Gly Ser Glu
         370                 375                 380

Gly Pro Lys Ile Leu Gln Lys Lys Gly Asp Ser Ser Asn Ala Ala Ala
385                 390                 395                 400

Glu Ala Lys Lys Glu Asn Lys Ser Asp Gly Ala Ser Lys Ala Leu
                405                 410                 415

Ser Lys Phe Ile Asp Pro Ser Leu Ser Trp Glu Asp Ile Ala Lys Met
            420                 425                 430

Arg Lys Leu Thr Lys Leu Pro Ile Val Ile Lys Gly Val Gln Arg Ala
            435                 440                 445

Glu Asp Ala Val Arg Ala Ala Gln Met Gly Cys Gln Gly Val Val Leu
            450                 455                 460

Ser Asn His Gly Gly Arg Gln Leu Asp Phe Ser Arg Ala Pro Ile Glu
465                 470                 475                 480

Val Leu Ala Glu Thr Met Pro Ile Leu Lys His His Gly Leu Asp Lys
                485                 490                 495

Asn Phe Asp Val Phe Val Asp Gly Gly Ile Arg Arg Gly Thr Asp Ile
            500                 505                 510

Leu Lys Ala Leu Cys Leu Gly Ala Thr Gly Val Gly Leu Gly Arg Pro
            515                 520                 525

Phe Leu Tyr Ala Asn Ser Cys Tyr Gly Arg Asp Gly Val Ala His Ala
            530                 535                 540

Ile Asp Ile Ile Thr Lys Glu Leu Glu Met Ser Met Arg Leu Leu Gly
545                 550                 555                 560

Val Ser Lys Ile Glu Asp Leu Asn Pro Gly Phe Leu Asp Leu Gln Ser
                565                 570                 575

Leu His Ala Arg Ser Val Leu Val Ala Lys Asp Ala Leu Tyr Glu Asn
            580                 585                 590

Ser Tyr Lys Glu Pro Gln Leu Ala Lys Phe Leu Ile Asp Asp Asp
            595                 600                 605

<210> SEQ ID NO 5
<211> LENGTH: 375
<212> TYPE: DNA
<213> ORGANISM: Artificial Sequence
<220> FEATURE:
<223> OTHER INFORMATION: promotor region of g2947 allele 1

<400> SEQUENCE: 5
atatattttg gctgacattg taattagatg agatccacaa ttttctttt gtttgactgt        60 tcgatatgga gaaggtggga tgcactatta ttatattcag aagtttattt gtacagttta    120
aagaacaaat agtggctaat cctatcctcg gactaaaaaa aatcgttcac ttctatccta    180
ctgtaaatct tatgaaaatg atgtaattca tatagttact atattttctt tcttttagaa    240 acttatgat atatatatat atataaaagg actaatcacc caactctcaa attcattaaa      300
aagaaatatg tttctatcat cttcttttct tattatacct cgtctaataa taaaaccaaa    360
caattttctg taaag                                                      375

<210> SEQ ID NO 6
<211> LENGTH: 375
<212> TYPE: DNA
<213> ORGANISM: Artificial Sequence
<220> FEATURE:
<223> OTHER INFORMATION: promotor region of g2947 allele 2

<400> SEQUENCE: 6

| | | |
|---|---|---|
| atatattttg gctgacattg taattagatg agatccacaa ttttctttt gtttgactgt | 60 | |
| tcgatatgga gaaggtggga tgcactatta ttatattcag aagtttattt gtacagcttg | 120 | |
| aagaacaaat agtggctaat cctatcctcg gactaaaaaa aattgttcac ttttatccta | 180 | |
| ctgtaaatct tatgaaaatg atgtaattca tatagttact atattttctt tcttttagaa | 240 | |
| acttcatgat atatatatat atataaaagg actaatcacc caactctcaa atttattaaa | 300 | |
| aagaaatatg tttctatcat cttcttttct tattatacct tctctaataa taaaaataaa | 360 | |
| caactttctg taaag | 375 | |

<210> SEQ ID NO 7
<211> LENGTH: 963
<212> TYPE: DNA
<213> ORGANISM: Artificial Sequence
<220> FEATURE:
<223> OTHER INFORMATION: ldh gene from Lactobacillus plantarum

<400> SEQUENCE: 7

| | | |
|---|---|---|
| atgtcttcta tgccaaatca tcaaaaagtt gttttggttg gtgatggtgc tgttggttct | 60 | |
| tcttatgctt ttgctatggc tcaacaaggt attgctgaag aatttgttat tgttgatgtt | 120 | |
| gttaaagata gaactaaagg tgatgctttg gatttggaag atgctcaagc ttttactgct | 180 | |
| ccaaaaaaaa tttattctgg tgaatattct gattgtaaag atgctgattt ggttgttatt | 240 | |
| actgctggtg ctccacaaaa accaggtgaa tctagattgg atttggttaa taaaaatttg | 300 | |
| aatattttgt cttctattgt taaaccagtt gttgattctg ttttgatgg tatttttttg | 360 | |
| gttgctgcta atccagttga tattttgact tatgctactt ggaaattttc tggttttcca | 420 | |
| aaagaaagag ttattggttc tggtacttct ttggattctt ctagattgag agttgctttg | 480 | |
| ggtaaacaat ttaatgttga tccaagatct gttgatgctt atattatggg tgaacatggt | 540 | |
| gattctgaat tgctgcttta ttctactgct actattggta ctagaccagt tagagatgtt | 600 | |
| gctaaagaac aaggtgtttc tgatgatgat ttggctaaat ggaagatgg tgttagaaat | 660 | |
| aaagcttatg atattattaa tttgaaaggt gctactttt atggtattgg tactgctttg | 720 | |
| atgagaattt ctaaagctat tttgagagat gaaaatgctg ttttgccagt tggtgcttat | 780 | |
| atggatggtc aatatggttt gaatgatatt tatattggta ctccagctat tattggtggt | 840 | |
| actggtttga acaaattat tgaatctcca ttgtctgctg atgaattgaa aaaaatgcaa | 900 | |
| gattctgctg ctactttgaa aaaagttttg aatgatggtt tggctgaatt ggaaaataaa | 960 | |
| taa | 963 | |

<210> SEQ ID NO 8
<211> LENGTH: 988
<212> TYPE: DNA
<213> ORGANISM: Artificial Sequence
<220> FEATURE:
<223> OTHER INFORMATION: g4423 5-UTR allele 1

<400> SEQUENCE: 8

| | | |
|---|---|---|
| gttaactcag ttttctctct ttccctccac cccacgttac tctgcgaaca aaaatacgca | 60 | |
| cagaatgaac atctgattga ttaatattta tatattactt agtggcaccc ctacaaacaa | 120 | |
| accaattttg aatatttctc accatcatga tatttattta gggcaagaat tcatgtaca | 180 | |
| tacgtgcgtg tactgcatag ttttgttata tgtaaataac cagcaatata tcaccaatga | 240 | |
| taaatgctca gtaattttat tggaaccaaa atagtttcag taatcaaata atacaataac | 300 | |

| | |
|---|---|
| taacaagtgc tgattataca acagctgtta acaacacaaa cacgctctct tctattctct | 360 |
| tccctgcttg ttcgtgtggt atattcccga atttgcaatt tagaaattat attttttaaa | 420 |
| agaattgttc tccatttttct ggtagtcgta agtggcaaat tggatcataa gacacaatct | 480 |
| tgttagttcg actgctaaca ccagacaaga ccgaacgaaa acagaaaaaa aagataattt | 540 |
| tgttattctg ttcaattctc tctctctttt taaggtatct ttacattaca ttacatatcc | 600 |
| caaattacaa caagagcaag aaatgaagca caacaacacg ccatctttcg tgattatttt | 660 |
| atcatttcta tatcgtaact aaattaacaa atgctatgtt tcttaatttt taatgataaa | 720 |
| tctaactgct accttaattt ctcatggaaa gtggcaaata cagaaattat atattcttat | 780 |
| tcatttttctt ataattttta tcaattacca aatatatata aatgcaatta attgattgtt | 840 |
| cctgtcacat aatttttttt gtttgttacc tttattctttt atccatttag tttagttctt | 900 |
| atatctttct tttctatttc tctttttcgt ttaatctcac cgtacacata tatatccata | 960 |
| tatcaataca aataaaaatc atttaaaa | 988 |

<210> SEQ ID NO 9
<211> LENGTH: 961
<212> TYPE: DNA
<213> ORGANISM: Artificial Sequence
<220> FEATURE:
<223> OTHER INFORMATION: g4423 5-UTR allele 2

<400> SEQUENCE: 9

| | |
|---|---|
| gttaactcag ttttctctct ttccctccac cccacgttac tctgcgaaca aaaaatacgc | 60 |
| acagaatgaa catctgattg attaatattt atatattact cagtggcacc cctacaaaca | 120 |
| aaccaatttt gaatattgtt caccatcatg atatttattt agggcaagaa tttcatgtac | 180 |
| atacgtgcgt gtactgcata gttttgttat atgaaaataa ccagcaatat atcaccaatg | 240 |
| aataaattct caataattta tttggaacca aataatgcaa taactagcaa actaagtggt | 300 |
| gattatacaa cagctgttaa caacacaaac atacgctctc ttctattatc tcttcccctgc | 360 |
| ttgttcgtgt ggtatattca cgaatttgca atttagaaat tatattttttt aaaagaattg | 420 |
| ttctccattt tctggtagtc gtaagtggca aattggatca taagacacaa tcttgttagt | 480 |
| tcgactgcta acaccagaca acaccgaacg aaaacaagaa aaataatta ttctctctct | 540 |
| ttttaaggta tcttacatta catatcccaa attacaacaa gagcaagaaa tgaggcacaa | 600 |
| caacacacca tcatctttcg tgattatttt tatcatttct atcatgtaat taaattaaca | 660 |
| aatgttaagt ttattaattt ttaatgataa atctagttgc taccttaatt tctcatggaa | 720 |
| agtggcaaat actgaaatta tttaattcta cttttcatttt cttataattt ttatcaatta | 780 |
| ccaaatatat ataaatgcaa ttaattgatt gttcctgtca cataattttt tttgtttgtt | 840 |
| accttttattc tttatccatt taatttattt cttgtatctt tcttttctat ttctcttttc | 900 |
| tgtttaatct caccgtacac atatatatcc atatatcaat acaaataaaa atcatttaaa | 960 |
| a | 961 |

<210> SEQ ID NO 10
<211> LENGTH: 1017
<212> TYPE: DNA
<213> ORGANISM: Artificial Sequence
<220> FEATURE:
<223> OTHER INFORMATION: g4423 3-UTR allele 1

<400> SEQUENCE: 10

| | |
|---|---|
| taagtcattt aatttattct tttagaatat atttattttg tctttatttt tgaaatgtta | 60 |

```
atagtctttt ttttttactt tgaacaaaaa aaagtaaaat taaaacttat ctttatatacg    120 cttttaaaca ttaaactcgt taacgaatta tataatgatt ttatcgaact actttatgtt    180
tttttaatag aataatcttc tttattaata taacttacta cttcttaatc ttgttgtcct    240
ccattcgaaa ctcgagtgga acattttctg agtatctctc gcgtctgttc gtaccgtttt    300
tccaatttct ttcgggaaac ggaactggac gcattttatt tgactgttga aagggagatt    360
taatatttat atagcgagat ataacaacta acttataagt ttacacaggc tgttatcaca    420
tatatatata tatatcaaca gaggactagc tcactagact aacattagat atgtcgatgc    480
tgaaccgttt gtttggtgtt agatccattt cacaatgtgc tactcgttta caacgttcta    540
cagggacaaa tatatcagaa ggtccactaa gaattattcc acaattacaa actttctatt    600
ctgctaatcc aatgcatgat aacaatatcg acaagctaga aaatcttcta cgtaaatata    660
tcaagttacc aagtacaaac aatttattga agacacatgg aatacatct acagaaattg    720 atccaacaaa attattacaa tcacaaaatt cttcacgtcc tttatggtta tcattcaagg    780
attatacagt gattggaggt ggttcacgtt taaaacctac tcaatacacg gaacttttat    840
ttctattgaa taaactacat agtatcgatc cacaattaat gaatgatgat attaagaacg    900
aattagctca ttattataag aatacttcac aggaaactaa taaagtcacc atccctaaat    960
tggatgaatt cggtagaagt attggaatcg gtagaaggaa atccgcaact gcaaaag     1017
```

<210> SEQ ID NO 11
<211> LENGTH: 1018
<212> TYPE: DNA
<213> ORGANISM: Artificial Sequence
<220> FEATURE:
<223> OTHER INFORMATION: g4423 3-UTR allele 2

<400> SEQUENCE: 11

```
taagtcattt aatttattct tttagaatat atttattttg tctttatttt tgaaatgtta     60
atagtctttt ttttactttg aaaaaaaaaa aaagtaaaat taaacttatc ttatatacgc    120
ttttaaacat taaactcgtt aacgaattat ataatgattt tatcgaacta ctttatgttt    180
ttttaataga ataatcttct ttattaatat aacttactac ttcttaatct tgttgtcctc    240
cattcgaaac tcgagaggaa caatttctga gtctctctcg cacccttcg tacgtaccgt    300 ttttccaatt tctttcggga aacggaactg gacgcatttt atttgactgt tgaagggag     360 atttaatatt tatatagaga gatataacaa ctaacttata agtttataca ggctgttatc    420
acatatatat atatatcaac agaggactag ctcaatagaa taacattaga tatgtcgatg    480
ctgaaccgtt tgtttggtgt tagatccatt tcacaatgtg ctactcgttt acaacgttct    540
acagggacaa atatatcaga aggtccacta agaattattc cacaattaca aactttctat    600
tctgctaatc caatgcatga taacaatatc gacaagctag aaaatcttct acgtaaatat    660
atcaagttac caagtacaaa taacttattg aagacacatg gaatacatc tacagaaatc    720 gatccaacaa aattattaca atcacaaaat tcttcacgtc ctttatggtt atcattcaag    780
gattatacag tgattggagg tggttcacgt ttaaaaccta ctcaatacac agaactttta    840
tttctattga ataaactaca tagtatcgat ccacaattaa tgaatgatga tattaagaac    900
gaattagctc attattataa gaatacttca caggaaacta ataaagtcac catccctaaa    960
ttggatgaat tcggtagaag tattggaatc ggtagaagga aatccgcaac tgcaaaag    1018
```

<210> SEQ ID NO 12

```
<211> LENGTH: 19
<212> TYPE: DNA
<213> ORGANISM: Artificial Sequence
<220> FEATURE:
<223> OTHER INFORMATION: primer

<400> SEQUENCE: 12
gcaggatatc agttgtttg                                                  19

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
aataccttgt tgagccatag                                                 20

<210> SEQ ID NO 14
<211> LENGTH: 234
<212> TYPE: DNA
<213> ORGANISM: Artificial Sequence
<220> FEATURE:
<223> OTHER INFORMATION: 3' terminator region of g2947 allele 1

<400> SEQUENCE: 14
ttgtgactct atggagttta cctattttat ataccactat atcacaaaaa gtaataacaa      60
cttttcaaat ataatacaat attcaataaa tatatttata tattctaaaa tctacgtttt     120
tctctttctt aaaaaaataa acaaactgac cctttcaatc ttcaatgtga tactttactt     180
attttatttc attacacaga aaggtataaa tatatacata acttaatggt ttat           234

<210> SEQ ID NO 15
<211> LENGTH: 234
<212> TYPE: DNA
<213> ORGANISM: Artificial Sequence
<220> FEATURE:
<223> OTHER INFORMATION: 3'-terminator region of g2947 allele 2

<400> SEQUENCE: 15
ttgtgactct atggagttta cctattttat ataccactgt atcacaaaaa gtaataacaa      60
cttctcaaat ataatacaat atttaataaa tatatttata tattctaaaa tctacgtttt     120
tctctttctt aaaaaaataa acaaactgac cctttcaatc ttcaatgtga tactttactt     180
attttatttc attacacaga aaggtataaa tatatacata acttaatggt ttat           234

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
ctagttgtgg ttccttgtat                                                 20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
```
gaaaataaat ccgatggtgc 20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
tgtttgactg ttcgatatgg 20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gaaaataaat ccgatggtgc 20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
tgtttgactg ttcgatatgg 20

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
gaagattgaa agggtcagt 19

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gactaatcac ccaactctca 20

<210> SEQ ID NO 23
<211> LENGTH: 18
<212> TYPE: DNA
<213> ORGANISM: Artificial Sequence
<220> FEATURE:
<223> OTHER INFORMATION: primer

<400> SEQUENCE: 23
atcgccgagg tactagag 18